US006172058B1

(12) United States Patent
Tercero et al.

(10) Patent No.: US 6,172,058 B1
(45) Date of Patent: *Jan. 9, 2001

(54) COMPOUNDS WITH PHARMACEUTICAL PROPERTIES

(75) Inventors: Concepción Pedregal Tercero; Ivan Collado Cano, both of Madrid; Angel Mazón Ruiz, Elche, all of (ES)

(73) Assignee: Lilly, SA, Madrid (ES)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/054,874

(22) Filed: Apr. 3, 1998

(30) Foreign Application Priority Data

Apr. 8, 1997 (ES) .................................... 9700736

(51) Int. Cl.[7] ...................... C07C 229/28; A01N 43/46; A01N 43/42; A61K 31/54; A61K 31/535

(52) U.S. Cl. .................... 514/217; 562/433; 562/435; 562/441; 562/442; 562/444; 562/451; 562/456; 562/458; 514/226.2; 514/229.8; 514/297; 514/437; 514/454; 514/561; 514/567; 540/479; 540/587; 544/58.1; 544/58.2; 544/102; 546/104; 549/26; 549/27; 549/388

(58) Field of Search ...................... 562/433, 435, 562/441, 442, 444, 451, 456, 458; 514/217, 226.2, 229.8, 297, 437, 454, 561, 567; 540/479, 587; 544/58.1, 58.2, 102; 546/104; 549/29, 27, 388

(56) References Cited

U.S. PATENT DOCUMENTS

| 4,959,463 | 9/1990 | Froehler et al. . |
| 4,959,493 | 9/1990 | Ohfume et al. ...................... 562/506 |

FOREIGN PATENT DOCUMENTS

| 06179643 | 6/1994 | (JP) . |
| 8-301825 | 11/1996 | (JP) ........................................ 229/46 |
| WO 95/15940 | 6/1995 | (WO) . |
| WO 96/07405 | 3/1996 | (WO) . |
| WO 97/19049 | 5/1997 | (WO) . |
| WO 9800391-A1 | 1/1998 | (WO) . |

OTHER PUBLICATIONS

Hayashi, Y. et al., Br. J. Pharmacol., 1992, 107, 539–543.
Ishida, M. et al., Br. J. Pharmacol., 1993, 109, 1169–1177.
Ishida, M. et al., Eur. J. Pharmacol., 1994, 268, 267–270.
Pellicciari, R. et al., J. Med. Chem., 1996, 39, 2259–2269.
Ornstein, P. L. et al., J. Med. Chem., 1998, 41, 346–357.
Ornstein, P. L. et al., J. Med. Chem., 1998, 41, 358–378.
Collado, I., et al., Tetrahedron Lett., 1997, 38, 2133–2136.
Wright, R. A., et al., J. Neurochem., 1994, 63, 938–945.
Monn, J. A. et al., J. Med. Chem., 1997, 40, 528–537.
Shimamoto, K., et al., Synlett, 1993, 919–920.
Shimamoto, K., et al., J. Med. Chem., 1996, 39, 407–423.
Shimamoto, K., et al., Tetrahedron Lett., 1990, 31, 4049–4052.
Shimamoto, K., et al., Bioorg. Med. Chem. Lett., 1996, 6, 2381–2386.
Ohfume, et al., Bioorg. Med. Chem. Lett., 1993, 3, 15–18.
Marinozzi, M. et al., Bioorg. Med. Chem. Lett., 1996, 6, 2243–2246.
Martin, S. F., et al., Tetrahedron Lett., 1990, 31, 4731–4734.
Ma. D., et al., Tetrahedron Asymm., 1997, 8, 889–893.
Marinozzi, M., et al., Il Farmaco., 1996, 51, 121–124.
Marinozzi, M., et al., Il Farmaco., 1995, 50, 327–331.
Joucla, M. et al., Tetrahedron Lett., 1986, 27, 1677–1680.
Taguchi, T., et al., Biomed. Front. Fluor. Chem., 1996, 639, 73–82.
Ishia, M., et al., Poster P13.2.2, Jul. 26, 1994, XIIth International Congress of Pharmacology, Jul. 24–29, 1994, Montreal, Canada.
Miyamoto, M., et al., Poster P13.2.1, Jul. 26, 1994, XIIth International Congress of Pharmacology, Jul. 24–29, 1994, Montreal, Canada.
Wilsch V. W., et al., Poster, 115.04, Sep. 8, 1994, 17th Annual Meeting European Neuroscience Association, Sep. 4–8, 1994, Vienna, Austria.

Primary Examiner—Johann Richter
Assistant Examiner—Brian J. Davis
(74) Attorney, Agent, or Firm—Arvie J. Anderson; Suzanne M. Harvey; Martin A. Hay

(57) ABSTRACT

A pharmaceutical compound of the formula (I)

$$\begin{array}{c} R^1 \\ H_2N \quad CO_2H \\ \diagup 3 \diagdown \\ HO_2C \diagdown 2 \diagup 1 \diagup R^2 \end{array}$$

in which $R^1$ is $C_{1-10}$ alkyl, $C_{2-10}$ alkenyl, $C_{2-10}$ alkynyl, $C_{3-10}$ cycloalkyl, $C_{3-10}$ cycloalkyl-$C_{1-10}$ alkyl, $C_{3-10}$ cycloalkyl-$C_{2-10}$ alkenyl, $C_{3-10}$ cycloalky-$C_{2-10}$ alkynyl, optionally substituted phenyl-$C_{1-10}$ alkyl, optionally substituted phenyl-$C_{2-10}$ alkenyl, optionally substituted phenyl-$C_{2-10}$ alkynyl, optionally substituted naphthyl, optionally substituted naphthyl-$C_{1-10}$ alkyl, $C_{1-10}$ alkoxy-$C_{1-10}$ alkyl, $C_{3-10}$ cycloalkoxy-$C_{1-10}$ alkyl, optionally substituted heterocyclyl, optionally substituted heterocyclyl-$C_{1-10}$ alkyl, optionally substituted phenyl fused to $C_{5-10}$ cycloalkyl, optionally substituted tricyclic, optionally substituted tricyclic-$C_{1-10}$ alkyl, or [optionally substituted phenyl(CH$_2$)$_n$]$_2$-$C_{1-10}$ alkyl, where n is 0 or 1 to 4, and $R^2$ is hydrogen or one of the values for $R^1$; or a salt or ester thereof.

13 Claims, No Drawings

COMPOUNDS WITH PHARMACEUTICAL PROPERTIES

This invention relates to novel chemical compounds and their use as pharmaceuticals.

It is well known that excitatory neurotransmission in the mammalian central nervous system is primarily mediated by the amino acid, L-glutamate, acting on ionotropic and metabotropic receptors.

Certain cyclopropyl glycine derivatives are described as having useful properties in modulating the activity of such receptors as, for example, in U.S. Pat. No. 4,959,493 (Suntory Ltd) WO 96/07405 (Eli Lilly & Company) and WO 95/15940 (University of Bristol).

The present invention provides a compound of the formula:

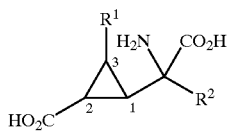

(I)

in which $R^1$ is $C_{1-10}$ alkyl, $C_{2-10}$ alkenyl, $C_{2-10}$ alkynyl, $C_{3-10}$ cycloalkyl, $C_{3-10}$ cycloalkyl-$C_{1-10}$ alkyl, $C_{3-10}$ cycloalkyl-$C_{2-10}$ alkenyl, $C_{3-10}$ cycloalky-$C_{2-10}$ alkynyl, optionally substituted phenyl-$C_{1-10}$ alkyl, optionally substituted phenyl-$C_{2-10}$ alkenyl, optionally substituted phenyl-$C_{2-10}$ alkynyl, optionally substituted naphthyl, optionally substituted naphthyl-$C_{1-10}$ alkyl, $C_{1-10}$ alkoxy-$C_{1-10}$ alkyl, $C_{3-10}$ cycloalkoxy-$C_{1-10}$ alkyl, optionally substituted heterocyclyl, optionally substituted heterocyclyl-$C_{1-10}$ alkyl, optionally substituted phenyl fused to $C_{5-10}$ cycloalkyl, optionally substituted tricyclic, optionally substituted tricyclic-$C_{1-10}$ alkyl, or [optionally substituted phenyl$(CH_2)_n]_2$-$C_{1-10}$ alkyl, where n is 0 or 1 to 4, and $R^2$ is hydrogen or one of the values for $R^1$; or a salt or ester thereof.

The compounds of the invention have been found to be active in tests indicative of their use in the treatment of diseases of the central nervous system such as neurological diseases, for example neurodegenerative diseases, and as antipsychotic, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in the form of diastereomeric pairs and individual enantiomers.

In the above general formula, a $C_{1-10}$ alkyl group can be straight or branched chain, such as, for example, methyl, ethyl, propyl, isopropyl, butyl and isobutyl, and is referably methyl or ethyl. A $C_{2-10}$ alkenyl group includes, or example, vinyl, prop-2-enyl, but-3-enyl, pent-4-enyl and isopropenyl, and an alkenyl group can contain more than one double bond and, in addition, one or more triple bonds. A preferred alkenyl group is of the formula R'—CH=CH— where R' is $C_{1-4}$ alkyl. A $C_{2-10}$ alkynyl group includes, for example, prop-2-ynyl, but-3-ynyl, pent-4-ynyl and oct-7-ynyl, and is preferably of the formula R'C≡C- where R' is $C_{1-4}$ alkyl. A $C_{3-10}$ cycloalkyl group is preferably, for example, cyclopropyl, cyclobutyl, cyclopentyl or cyclohexyl and these groups may optionally be substituted by one or two $C_{1-4}$ alkyl, for example methyl, substituents, or can be a bicyclo-system as, for example, bicyclooctane or adamantyl. Furthermore, the cycloalkyl group may be fused with phenyl or heterocyclyl.

In the above general formula, an optionally substituted phenyl or optionally substituted naphthyl is optionally substituted with, for example, one or more substituents, preferably 1 to 3 substituents, selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino, $C_{1-4}$ acylamino, $C_{1-4}$ alkylthio, optionally substituted phenyl and phenoxy. An optionally substituted phenyl-$C_{1-10}$ alkyl group is one such group linked through an alkylene chain, for example, phenyl-$(CH_2)$n where n is 1 to 10, and a most preferred example is benzyl. An optionally substituted phenyl-$C_{2-10}$ alkenyl is one such phenyl group linked through an alkenylene chain derived from an alkenyl group as defined above, and preferably of the formula phenyl-$(CH_2)_n$CH=CH—where n is 1 to 4. An optionally substituted phenyl-$C_{2-10}$ alkynyl group is an optionally substituted phenyl group linked through an alkynylene chain derived from an alkynyl group as defined above, and preferably of the formula phenyl-$(CH_2)_n$C≡C— where n is 1 to 4.

A heterocyclic group is a cyclic group of one or more rings containing one or more hetero atoms, and can be aromatic or non-aromatic. A substituted heterocyclyl group can be substituted with one or more substituents, preferably 1 to 3 substituents, as defined for substituted phenyl. An aromatic heterocyclic group includes a 5 to 7 membered ring containing one to four heteroatoms selected from oxygen, sulfur and nitrogen, and can be fused with a benzene ring or a 5 to 6 membered ring containing from one to four heteroatoms selected from oxygen, sulfur and nitrogen. Examples are thienyl, furyl, oxazolyl, isoxazolyl, thiazoyl, isothiazolyl, imidazolyl, benzofuryl, benzothiophenyl, benzimidazolyl, benzoxazolyl, benzothiazolyl and indolyl.

A non-aromatic heterocyclic group includes a 4 to 7 membered ring containing one or two heteroatoms selected from oxygen, sulphur and nitrogen, for example, pyrrolidinyl, piperidinyl, tetrahydrofuranyl, tetrahydropyranyl, piperazinyl, morpholinyl, or thiomorpholinyl.

An optionally substituted tricyclic group comprising three fused rings which can optionally be substituted with one or more substituents, for example, 1 to 3 substituents as defined for substituted phenyl. The fused rings can be aromatic or non-aromatic and can contain, for example, one or two heteroatoms selected from oxygen, sulphur and nitrogen. A preferred tricyclic group is of the formula

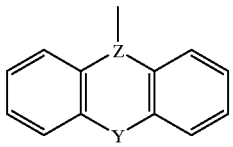

where Z is

or

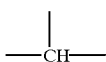

and Y is —O—, —S—, —SO—, —SO$_2$—, —CH=CH—, —(CH$_2$)$_p$— where p is 1, 2 or 3. A particularly preferred example is 9-xanthyl. An optionally substituted tricyclic-C$_{1-10}$ alkyl group is one such group attached to a C$_{1-10}$ alkyl, and a particularly preferred example is 9-xanthylmethyl.

Preferred examples of R$^1$ and R$^2$ are C$_{1-10}$ alkyl, C$_{3-10}$ cycloalkyl-C$_{1-10}$ alkyl, optionally substituted phenyl-C$_{1-10}$ alkyl, C$_{1-10}$ alkoxy-C$_{1-10}$ alkyl, optionally substituted heterocyclyl-C$_{1-10}$ alkyl, optionally substituted phenyl fused to C$_{5-10}$ cycloalkyl and [optionally substituted phenyl(CH$_2$)$_n$]$_2$-C$_{1-10}$ alkyl.

Especially preferred examples are C$_{1-10}$ alkyl, C$_{3-10}$ cycloalkyl-C$_{1-4}$ alkyl, phenyl-C$_{1-4}$ alkyl, diphenyl C$_{1-4}$ alkyl, C$_{1-4}$ alkoxy-C$_{1-4}$alkyl, and 9-xanthyl-C$_{1-4}$ alkyl, and particularly preferred instances of R$^1$ and R$^2$ are methyl, ethyl, propyl, butyl, pentyl, hexyl, heptyl, octyl, nonyl, methoxymethyl, methoxyethyl, ethoxymethyl, ethoxyethyl, butoxyethyl, benzyl, phenethyl, diphenylmethyl, diphenylethyl and 9-xanthylmethyl.

A further preferred group of compounds is one of formula (I) in which R$^1$ is C$_{1-6}$ alkyl and R$^2$ is 9-xanthylmethyl.

A particularly preferred group is where R2 is H or xanthylmethyl. As mentioned above, the compounds of formula (I) can exist in enantiomeric forms and there are at least four chiral centres in the molecule. Substituents at the 1 and 2 position can be in both cis and trans relationship, the trans form being preferred. Thus, a preferred group of compounds has the following structure:

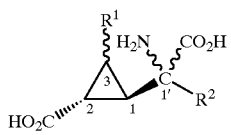

Furthermore, the amino acid moiety preferably has the natural amino configuration.

The present invention includes pharmaceutically acceptable salts of the formula (I) compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

It is, of course, possible to prepare salts of the compounds of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable acceptable, acid addition salts, or are useful for identification, characterisation or purification.

The compounds can be utilised in ester form, such esters being aliphatic or aromatic such as, for example, alkyl and phenolic esters. The most preferred esters are alkyl esters derived from C$_{1-4}$ alkanols, especially methyl and ethyl esters.

The invention also comprises a process for preparing a compound according to formula (I), or a pharmaceutically acceptable salt thereof which comprises:

(a) hydrolyzing a compound of formula

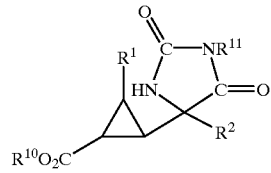

(III)

in which R$^{10}$ and R$^{11}$ each represent hydrogen, a C$_{1-4}$ alkyl group, a phenyl C$_{1-4}$ alkyl group in which the phenyl group is unsubstituted or substituted by halo, C$_{1-4}$ alkyl, C$_{1-4}$ alkoxy or C$_{3-4}$ alkenyl; or (b) deprotecting a compound of formula

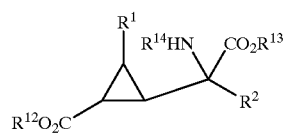

(III)

in which one or both of R$^{12}$ and R$^{13}$ is a carboxyl protecting group, and the other is hydrogen, and R$^{14}$ is hydrogen or an amine protecting group;

followed when necessary by recovering a diastereomer or isomer of the compound, or forming a pharmaceutically acceptable ester or pharmaceutically acceptable salt thereof.

The invention also comprises a process for preparing a compound according to formula (I)where R$^2$ is H, which comprises:

(a) hydrolyzing a compound of formula (II')

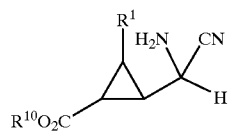

(II')

in which R$^{10}$ represents hydrogen, a C$_{1-4}$ alkyl group, a phenyl C$_{1-4}$ alkyl group in which the phenyl group is unsubstituted or substituted by halo, C$_{1-4}$ alkyl, C$_{1-4}$ alkoxy or C$_{3-4}$ alkenyl; or (b) deprotecting a compound of formula (III')

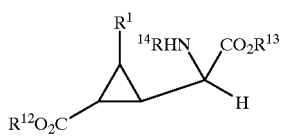

(III')

in which one or both of $R^{12}$ and $R^{13}$ is a carboxyl protecting group, and the other is hydrogen, and $R^{14}$ is hydrogen or an amine protecting group;
followed when necessary by recovering a diastereomer or isomer of the compound, or
forming a pharmaceutically acceptable ester or pharmaceutically acceptable salt thereof.

The protection of carboxylic acid group, is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-l-en-3-yl.

Examples of amine protecting groups include acyl groups, such as groups of formula $R^{15}CO$ in which $R^{15}$ represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted. Preferred amino protecting groups include BOC and benzyl.

Compounds of formula (II) are preferably hydrolyzed in the presence of a base, for example an alkali metal hydroxide such as lithium, sodium or potassium hydroxide, or an alkaline earth metal hydroxide such as barium hydroxide. The hydrolysis is conveniently performed in water at a temperature of from 100° C. to 250° C.

Compounds of formula (II') are preferably hydrolyzed in the presence of an acid, for example hydrochloric acid. The hydrolysis is conveniently performed in water at a temperature from 100° C. to 250° C.

Particular values for $R^{10}$, $R^{12}$ and $R^{13}$ are hydrogen, methyl, ethyl, n-propyl, n-butyl, t-butyl, benzyl, 4-methoxybenzyl, phenylethyl and phenylpropyl.

The compounds of formula (III) and (III') may be deprotected by conventional methods. Thus, an alkyl carboxyl protecting group may be removed by hydrolysis. The hydrolysis may conveniently be performed by heating the compound of in the presence of either a base, for example an alkali metal hydroxide such as lithium, sodium or potassium hydroxide, or an alkaline metal hydroxide, such as barium hydroxide or an acid such as hydrochloric acid. The hydrolysis is conveniently performed at a temperature in the range of from 100° C. to 300° C. An aralkyl carboxyl protecting group may conveniently be removed by hydrogenation. Thre aydrogenation may be effected by reacting the compound of formula (III) and (III')with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° C. to 100° C.

An acyl, amine protecting group is also conveniently removed by hydrolysis, for example as described for the removal of an alkyl carboxyl protecting group.

The compounds of formula (II) may be prepared by reacting a compound of formula (IV)

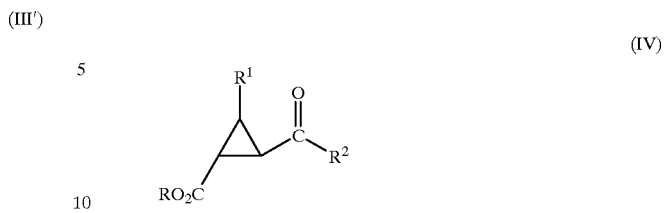

(IV)

in which R is a hydrogen atom or a $C_{1-6}$ alkyl group, with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C. If desired, the compounds of formula (II) may then be alkylated, for example using a compound of formula $R^{10}Cl$. The alkylated compounds are readily separated into their diastereomers.

The intermediate of formula (IV) can be prepared by reaction of a compound of formula

(V)

with, for example, a compound of the formula

EtOOC.CH$_2^{\oplus}$SMe$_2$ Br$^{\ominus}$ and DBU in an organic solvent such as, for example, chloroform or toluene. Reaction in chloroform gives a mixture of cis and trans isomers, whereas reaction in toluene results predominantly in the trans isomer.

Compounds of formula (V) can be prepared from dimethyl methylphosphonate according to the following reaction scheme:

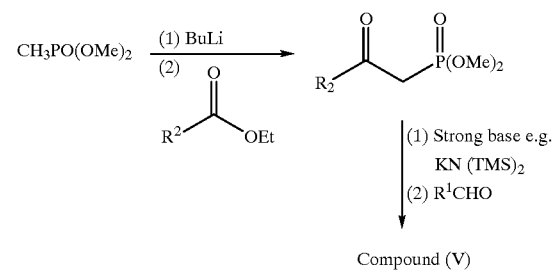

Compound (V)

Alternatively, compounds of formula (IV) can be prepared by reacting a compound of formula (VI)

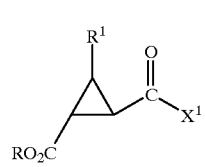

(VI)

in which $X^1$ is a leaving group such as, for example, chloro, and R is (1–6C) alkyl, with an appropriate organometallic reagent, optionally in the presence of a palladium(0) or a palladium (II) catalyst. Examples of appropriate organometallic reagents are organocadmium, organotin, organozinc and organocuprate reagents.

Palladium catalysis may be required for reactions of a compound of formula (VI) with organozinc and organotin reagents.

The reaction is conveniently performed in an organic solvent such as benzene at a temperature of from −50° C. to the reflux temperature of the solvent.

Compounds of formula (IV) in which $R^2$ is linked to the cyclopropyl group by an alkylene group of the formula —$(CH_2)_m$— where m is 2 to 10 may also be prepared by hydrogenating a compound of formula (VII)

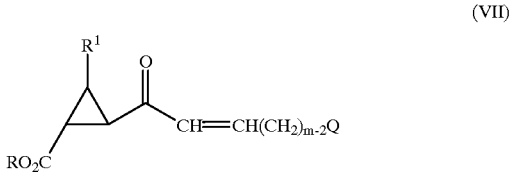

(VII)

The hydrogenation is conveniently performed in the presence of a palladium catalyst, such as palladium on charcoal, in an organic solvent such as ethanol.

Compounds of formula (VII) may be prepared by reacting a compound of formula (VIII)

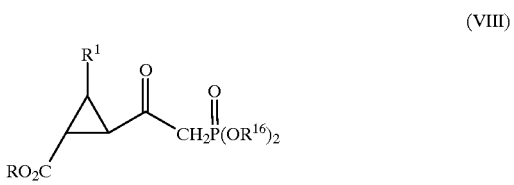

(VIII)

in which $R^{16}$ represents a $C_{1-4}$ alkyl group, such as methyl with an aldehyde of formula

OHC—$(CH_2)_{m-3}$—Q          (IX)

in the presence of a strong base, such as sodium hydride or sodium bis(trimethylsilyl)amide. The reaction is conveniently performed in the presence of an organic solvent such as tetrahydrofuran at about ambient temperature.

Compounds of formula (VIII) may be prepared by reacting a $C_{1-4}$ dialkyl methylphosphonate, such as dimethyl methylphosphonate with a strong base, such as butyl lithium, and then copper I iodide, followed by a compound of formula (VI).

Compounds of formula (III) in which $R^{13}$ represents a hydrogen atom may be prepared by hydrolyzing a compound of formula (X)

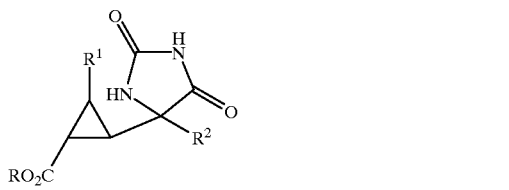

(X)

in which R represents a carboxyl protecting group.

Alternatively, the compounds of formula (III) may be prepared by reaction of a compound of formula (I) with an appropriate acyl halide or carbonyl chloride, in a solvent such as water, in the presence of a base such as sodium hydroxide, potassium carbonate, sodium bicarbonate or triethylamine. The corresponding substituted amine may then be reacted with a (1–6C) alkyl halide in the presence of a base such as potassium carbonate, sodium bicarbonate, triethylamine or di-i-propyl-N-ethylamine in a solvent such as dimethylformamide, dimethylsulfoxide or acetonitrile.

Alternatively, compounds of formula (III) may be prepared by reaction of a compound of formula (I) with a (1–6C) alcohol, in the presence of an acid catalyst such as hydrogen chloride or sulfuric acid, or a dehydrating agent such as thionyl chloride. The derived diester may then be reacted with an acyl halide, a carbonyl chloride or a carboxylic acid that is activated with a reagent such as dicyclohexylcarbodiimide, N-hydroxysuccinimide, or i-butylchloroformate, in the presence of a base such as triethylamine, di-i-propyl-N-ethylamine, pyridine or 4-N,N-dimethylaminopyridine, in a solvent such as tetrahydrofuran or dichloromethane.

The compounds of formula (VI) may be prepared by a method analogous to that described for the preparation of compounds of formula (II), starting from a compound of formula (IV) in which R represents an appropriate carboxyl protecting group.

When an isomer of a compound of formula (I) is desired, this may conveniently be prepared by starting from an isomer of a compound of formula (V). The compound of formula (VI) may then be converted into a compound of formula (I) by incorporating a step of separating the diastereomeric hydantoins. The diastereomeric hydantoins may be separated, for example, by chromatography, crystallisation or by reaction with a $C_{1-4}$ alkyl halide, a phenyl $C_{1-4}$ alkyl halide or a $C_{3-4}$ alkenyl halide, such as 4-methoxybenzyl chloride to afford a compound of formula (II) in which $R^{10}$ and $R^{11}$ are $C_{1-4}$ alkyl, phenyl ($C_{1-4}$ alkyl or $C_{3-4}$ alkenyl, followed by separating the resultant diastereomers by chromatography, and then removing the alkyl, phenylalkyl or alkyl groups, for example by reaction with ceric ammonium nitrate, or by direct hydrolysis of the hydantoin, such as by heating to about 200_C in a sealed vessel in the presence of sodium hydroxide.

The compounds of formula II' may be prepared by reacting a compound of formula IV'

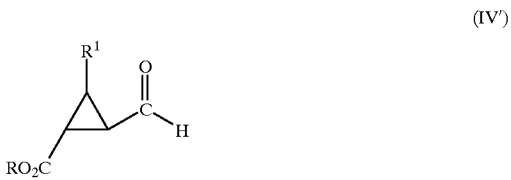

(IV')

with potassium cyanide, and ammonium chloride in acetonitrile. Conveniently the reaction is performed at a temperature from 35° C. to 150° C.

The intermediate of formula IV' can be prepared by reaction of a compound of formula

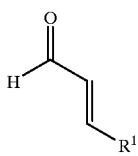

(V')

with, for example, a compound of the formula EtOOC—CH$_2$SMe$_2$ in an organic solvent such as, for example, chloroform or toluene by heating. Also enantiomerically pure diastereoisomers where R2 is H can be prepared by an asymmetric intramolecular ring-closure reaction, which controlled four stereogenic centres formation. A combination of two reactions were used. One, involved the formation of the cyclopropane ring by an intramolecular route using compounds with the general formula VI', and the other a stereocontrolled reaction with commercially available Schollkopf's bislactim ether VII'.

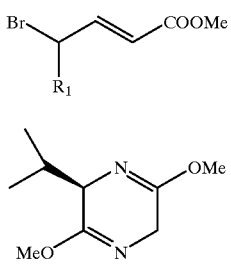

VI'

VII'

Bislactim ether VII' was lithiated with n-butyllithium in THF at −78° C. The lithiated enolate anion formed was then alkylated with trans methyl 4-bromo-4-alkyl-but-2-enoates (VI') to give the intermediate bislactim ether VIII'.

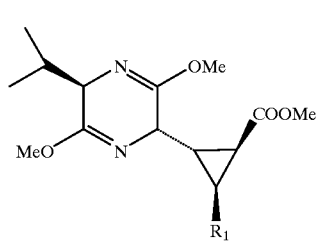

VIII'

A two stage hydrolysis of VIII', initially with 0.1N hydrochloric acid followed by 6N hydrochloric acid gave the desired crude which was purified by ion-exchange chromatography or treatment with propylene oxide.

Compounds VI' can be prepared from the corresponding alfa-bromo aldehyde with triethyl phosphono acetate by a Horner-Emmons reaction.

The compounds of the invention have pharmaceutical activity. They have been shown to possess affinity for metabotropic glutamate receptors. Excitatory amino acid and glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-asparate, AMPA, and kainate (Sommer B. and Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. and Conn J. P., Trends Pharacol. Sci. 14: 13–20, 1993). Metabotropic glutamate receptors can be selectively activated by 1S,3R-1-aminocyclopentane-1,3-dicarboxylic acid (1S,3R-ACPD).

The affinity of the compounds for metabotropic glutamate receptors has been demonstrated by the selective displacement of 1S,3R-ACPD-sensitive $^3$H-glutamate binding to rat brain cell membranes, a test for metabotropic glutamate receptor activity described by Schoepp D. D. and True R. A. (Neuroscience Lett. 145: 100–104, 1992). The preferred compounds of the invention have an IC50 value of less than 100 mM. The compounds also block the metabotropic glutamate receptor second messenger responses with IC50 values of less than 100 mM, including stimulation of phosphoinositide hydrolysis by 1S,3R-ACPD (Schoepp D. D., Johnson B. G., True R. A., and Monn J. A., Eur. J. Pharmacol.—Mol. Pharmacol. Section 207: 351–353, 1991) and reversal of 1S,3R-ACPD-induced inhibition of forskolin-stimulated cAMP formation (Schoepp D. D., Johnson B. G., and Monn J. A., J. Neurochem. 58: 1184–1186, 1992).

Based on studies of receptor mediated changes in intracellular second messengers, metabotropic glutamate receptor are either coupled to enhanced phosphoinositide hydrolysis or decreases in forskolin-stimulated cAMP formation. Thus, the preferred compounds of the invention have agonist activity since they evoked $^3$H-inositol phosphate formation in slices of the rat hippocampus as described by D. D. Schoepp et al., Journal of Neurochemistry 63: 769–772, 1994. They also inhibit forskolin (30 mM)-stimulated cAMP formation using slices of the rat hippocampus as described by D. D. Schoepp and B. G. Johnson, Neurochemistry International 22: 277–283 1993 and human mG1R2 expressing non-neuronal cells (D. D. Schoepp et al., Neuropharmacology, 1995).

A variety of physiological functions have been shown to be subject to influence by excessive or inappropriate stimulation of excitatory amino acid transmission. Thus the compounds of the invention are believed to be useful in treating a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. Compounds of the invention are thus indicated for the treatment of a variety of chronic neurological disorders, such as Alzheimer's disease, Huntington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of formula (I) or a pharmaceutically acceptable salt or ester thereof.

The compounds of the invention are also indicated for use in treating a variety of other neurological disorders in mammals that are associated with glutamate dysfunction, including muscular spasms, convulsions, migraine headaches, urinary incontinence, nicotine withdrawal, psychosis, (such as schizophrenia) opiate tolerance and withdrawal, drug withdrawal, smoking cessation anxiety, emesis, epilepsy, brain edema, chronic pain, and tardive dyskinesia. The compounds of the invention are also useful as antidepressant and analgesic agents. Thus, the present invention provides methods for treating these disorders which comprise administering to a patient in need thereof an effective amount of the compound of formula (I), or a pharmaceutically acceptable salt or ester thereof.

The dose of compound administered will be determined by the particular circumstances of the case, including the paticular compound administered, the method of administration, the condition being treated, and similar considerations. The compounds of the invention can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The compounds of the invention are preferably formulated prior to administration. Thus the invention also provides a pharmaceutical formulation comprising a compound of formula (I) in combination with one or more pharmaceutically-acceptable carriers, diluents, or excipients. The pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

The invention is illustrated by the following Preparations and Examples

PREPARATIONS

1) Phosphonates synthesis

To a solution of dimethyl methyl phosphonate (7.80 g, 63 mmol) in THF (63 mL) at −78_C. n-Butyllithium was dropwise added (69 mmol). After 15 minutes at this temperature the corresponding ester was added (31.5 mmol) in THF (30 mL) and the resulting solution stirred for 30 minutes at −78_C. The dry ice bath was removed and stirring continued for an additional hour. After quenching with saturated aqueous solution of $NH_4Cl$, the combined organic layer were dried over $Na_2SO_4$, evaporated and chromatographied using Hexane/Ethyl acetate 5:1 as eluent.

Dimethyl (4-Phenyl-2-oxobutyl) phosphonate

H NMR ($CDCl_3$) 7.24-7.17 (m, 5H), 3.74 (s, 3H), 3.68 (s, 3H), 3.00 (d, J=23.7 Hz, 2H), 2.89 (m, 4H). C NMR ($CDCl_3$) 200.8, 200.7, 140.3, 128.2, 128.1, 125.9, 52.8, 52.7, 45.3, 45.2, 42.4, 39.9, 29.1.

Dimethyl 3-(9-Xanthyl-2-oxopropyl) phosphonate

H NMR ($CDCl_3$) 7.28-7.00 (m, 8H), 4.60 (t, J=6.4 Hz, 1H), 3.65 (s, 3H), 3.60 (s, 3H), 4.14 (d, J=6.4 Hz, 2H), 4.50 (d, J=22.7 Hz, 2H).

2) Acyclic enones formation (All as the E isomer)

To the phosphonate (13.78 mmol) in anhidrous THE (37 mL) a 0.5M solution of KHMDS freshly prepared in toluene (12.72 mmol) was added at −78_C. After 20 minutes to this temperature the corresponding aldehyde (10.60 mmol) in TH1 (18 mL) was added and the temperature allowed to reach room temperature. After stirring 2 hours at ambient temperature the reaction was quenched with with saturated aqueous solution of $NH_4Cl$, the combined organic layer were dried over $Na_2SO_4$, evaporated and chromatographied using Hexane/Ethyl acetate 18:1 as eluent.

1-Phenyl-4-hexen-3-one

H NMR ($CDCl_3$) 7.45-7.20 (m, 5H), 6.84 (dt, J=6.8 and 15.8 Hz, H), 6.14 (dt, J=1.6 and 15.8 Hz, 1H), 3.00-2.80 (m, 4H), 1.88 (dd, J=1.6 and 6.8 Hz, 3H). C NMR ($CDCl_3$) 199.3, 142.8, 141.2, 131.8, 128.4, 128 .3, 125.9, 41.5, 29.9, 18.3.

1-Phenyl-4-decen-3-one

IR (film) 2928, 1674, 1630 $cm^{-1}$. H NMR ($CDCl_3$) 7.30-7.13 (m, 5H), 6.80 (dt, J=6.9 and 15.9 Hz, 1H), 6.10 (dt, J=1.4 and 15.9 Hz, pH), 2.97-2.81 (m, 4H), 2.20 (m, 2H), 1.50-1.35 (m, tH), 0.87 (t, J=7.6 Hz, 3H). C NMR ($CDCl_3$) 199.6, 147.8, 141.3, 130.2, 128.4, 128.3, 126.0, 41.5, 32.4, 31.3, 30.0, 27.7, 22.4, 13.9.

1,7-Diphenyl-4-hepten-3-one

IR (film) 2900, 1697, 1674, 1630, 1454, 698 $cm^{-1}$. H NMR ($CDCl_3$) 7.34-7.20 (m, 10H), 6.84 (dt, J=6.8 and 15.9 Hz, 1H), 6.10 (dt, J=1.4 and 15.9 Hz, 1H), 3.15-2.75 (m, 6H), 2.60-2.45 (m, 2H). C NMR ($CDCl_3$) 199.5, 146.3, 141.3, 140.6, 130.6, 128.5, 128.4, 128.3, 128.2, 126.2, 126.0, 41.7, 34.3, 34.1, 30.0.

1-Phenyl-4-tetradecen-3-one

IR (film) 2928, 1699, 1674, 1630 $cm^{-1}$. H NMR ($CDCl_3$) 7.35-7.15 (m, 5H), 6.81 (dt, J=6.9 and 15.9 Hz, 1H), 6.08 (dt, J=1.5 and 15.9 Hz, 1H), 2.97-2.80 (m, 4H), 2.18 (q, J=6.9 Hz, 2H), 1.26 (broad s, 14H), 0.88 (t, J=6.9 Hz, 3H). C NMR ($CDCl_3$) 199.5, 147.8, 141.2, 126.4, 126.3, 126.0, 41.5, 32.4, 31.8, 30.0, 29.4, 29.3, 29.2, 29.1.

1-(9-Xanthyl)-3-penten-2-one

IR (film) 3039, 1671, 1479, 1456, 1253 $cm^{-1}$. H NMR ($CDCl_3$) 7.28-7.10 (m, 8H), 6.65 (dt, J=6.8 and 15.8 Hz, 1H), 5.90 (dt, J=1.6 and 15.8 Hz, 1H), 4.68 (t, J=6.7 Hz, 1H), 2.90 (d, J=6.7 Hz, 2H), 1.77 (dd, J=1.6 and 6.7 Hz, 3H). C NMR ($CDCl_3$) 197.9, 152.2, 143.6, 132.4, 128.7, 127.8, 125.4, 123.4, 116.4, 50.6, 34.7, 18.3.

1-(9-Xanthyl)-3-hexen-2-one

IR (film) 2969, 1694, 1674, 1626, 1578, 1480, 1258 $cm^{-1}$. H NMR ($CDCl_3$) 7.30-6.85 (m, 8H), 6.75 (dt, J=6.6 and 15.8 Hz, 1H), 5.90 (dt, J=1.6 and 15.8 Hz, 1H), 4.66 (t, J=6.7 Hz, 1H), 2.90 (d, J=6.7 Hz, 2H), 2.10 (m, 2H), 0.94 (t, J=7.4 Hz, 3H). C NMR (CDCl$_3$) 198.2, 152.2, 149.8, 129.8, 128.7, 127.7, 125.3, 123.4, 116.4, 50.5, 34.7, 25.5, 12.0.

1-(9-Xanthyl)-3-hepten-2-one

IR (film) 2961, 1695, 1670, 1626, 1470, 1253 cm$^{-1}$. H NMR (CDCl$_3$) 7.27-6.97 (m, 8H), 6.59 (dt, J=6.9 and 15.9 Hz, 1H), 5.92 (dt, J=1.2 and 15.9 Hz, 1H), 4.66 (t, J=6.8 Hz, 1H), 2.90 (d, J=6.8 Hz, 2H), 2.05 (m, 2H), 1.30 (m, 2H), 0.83 (t, J=7.2 Hz, 3H). C NMR (CDCl$_3$) 198.2, 152.2, 148.4, 130.9, 128.7, 127.7, 125.3, 123.4, 116.4, 50.5, 34.8, 34.4, 21.1, 13.6.

1-(9-Xanthyl)-3-octen-2-one

IR (film) 2930, 1695, 1668, 1628, 1470, 1253 cm$^{-1}$. H NMR (CDCl$_3$) 7.28-6.98 (m, 8H), 6.45 (dt, J=6.9 and 15.9 Hz, 1H), 5.93 (dt, J=1.5 and 15.9 Hz, 1H), 4.66 (t, J=6.7 Hz, 1H), 2.90 (d, J=6.7 Hz, 2H), 2.05 (m, 2H), 1.30 (m, 4H), 0.85 (t, J=7.4 Hz, 3H). C NMR (CDCl$_3$) 198.1, 152.1, 148.6, 130.7, 128.7, 127.7, 125.3, 123.3, 116.4, 50.4, 34.7, 32.1, 29.9, 22.1, 13.7.

1-(9-Xanthyl)-3-nonen-2-one:

IR (film) 2928, 1670, 1479, 1254 cm$^{-1}$. H NMR (CDCl$_3$) 7.23-6.96 (m, 8H), 6.58 (dt, J=6.9 and 15.9 Hz, 1H), 5.93 (dt, J=1.4 and 15.9 Hz, 1H), 4.66 (t, J=6.7 Hz, 1H), 2.90 (d, J=6.97 Hz, 2H), 2.04 (m, 2H), 1.20 (m, 6H), 0.86 (t, J=7.2 Hz, 3H). C NMR (CDCl$_3$) 198.2, 152.2, 148.7, 130.7, 128.7, 127.7, 125.3, 123.3, 116.4, 50.5, 34.8, 32.4, 31.2, 27.5, 22.3, 13.9.

1-(9-Xanthyl)-3-decen-2-one:

IR (film) 2928, 1670, 1626, 1479, 1254 cm$^{-1}$. H NMR (CDCl$_3$) 7.28-6.97 (m, 8H), 6.59 (dt, J=6.9 and 15.8 Hz, 1H), 5.92 (dt, J=1.4 and 15.98 Hz, 1H) 4. 66 (t, J=6.7 Hz, 1H), 2.90 (d, J=6.97 Hz, 2H), 2.05 (m, 2H), 1.23 (m, 8H), 0.86 (t, J=7.0 Hz, 3H). C NMR (CDCl$_3$) 198.1, 152.1, 148.6, 130.7, 128.6, 127.7, 125.3, 123.3, 116.4, 50.4, 34.7, 32.4, 31.4, 28.7, 27.8, 22.4, 14.0.

1-(9-Xanthyl)-3-tridecen-2-one

IR (film) 2926, 1695, 1670, 1628, 1479, 1254 cm$^{-1}$. H NMR (CDCl$_3$) 7.27-6.97 (m, 8H), 6.58 (dt, J=6.8 and 15.9 Hz, 1H), 5.93 (dt, J=1.3 and 15.9 Hz, 1H), 4.66 (t, J=6.7 Hz, 1H), 2.90 (d, J=6.7 Hz, 2H), 2.03 (m, 2H), 1.22 (m, 14H), 0.87 (t, J=6.9 Hz, 3H). C NMR (CDCl$_3$) 198.1, 15 2.1, 148.6, 130.7, 128.7, 127.7, 125.3, 123.3, 116.4, 50.5, 34.7, 32.4, 31.8, 29.4, 29.3, 29.2, 29.0, 27.8, 22.6, 14.1.

1-(9-Xanthyl)-6phenyl-3-hexen-2-one

IR (KBr) 2930, 1647, 1681, 1458, 1258 cm$^{-1}$. H NMR (CDCl$_3$) 7.30-6.98 (m, 13H), 6.62 (dt, J=6.8 and 15.9 Hz, 1H), 5.94 (dt, J=1.4 and 15.9 Hz, 1H), 4.64 (t, J=6.7 Hz, 1H), 2.87 (d, J=6.7 Hz, 2H), 2.60 (m, 2H), 2.35 (m, 2H). C NMR (CDCl$_3$) 198.0, 152.1, 147.1, 140.5, 131.1, 128.7, 128.4, 128.2, 127.7, 126.1, 125.2, 123.3, 116.4, 50.6, 34.7, 34.1, 34.0.

1-(9-Xanthyl)-6-methyl-3-hexen-2-one

IR (KBr) 2920, 1661, 1479, 1257 cm$^{-1}$. H NMR (CDCl$_3$) 7.28-6.99 (m, 8H), 6.60 (dt, J=7.3 and 15.9 Hz, 1H), 5.94 (dt, J=1.4 and 15.9 Hz, 1H), 4.67 (t, J=6.8 Hz, 1H), 2.90 (d, J=6.8 Hz, 2H), 1.95 (m, 2H), 1.65 (m, 1H), 0.83 (d, J=6.7 Hz, 6H). C NMR (CDCl$_3$) 198.2, 152.2, 147.5, 131.8, 128.7, 127.8, 125.3, 123.4, 116.4, 50.5, 41.7, 34.9, 27.7, 22.6, 22.3, 14.1.

3) Cyclopropanation

The carbethoxymethyl dimethylsulfonium bromide (3.44 mmol) together with DBU (2.87 mmol) was stirred in chloroform (1.17 mL) for 30 minutes. Then the enone (2.87 mmol) in 1.7 mL of CHCl$_3$ was added and the resulting solution stirred overnight. The following day 0.5 equiv. of preformed ylide was added and stirred for 2 days. The crude mixture was diluted with dichloromethane (10 mL) and washed twice with 0.5N HCl (2×4 mL). The organic layer was dried over Na$_2$SO$_4$ and evaporated to yield a crude which was purified by column chromatography using ethyl acetate-hexane mixtures as eluent.

(1SR, 2SR, 3SR) Ethyl 2-acetyl-3-methyl cyclopropyl-1-carboxylate

Obtained using toluene as solvent. Hexane/Ethyl acetate, 9:1. IR (film) 1728, 1701, 1306, 1184 cm$^{-1}$. H NMR (CDCl$_3$) 4.13 (c, J=7.2 Hz, 2H), 2.40 (m, 5H), 1.85-1.70 (m, 1H), 145-1.20 (t, J=7.2 Hz, 3H+d, J=6.4 Hz, 3H). C NMR (CDCl$_3$) 205.6, 170.0, 60.7, 35.9, 30.9, 30.0, 25.8, 14.1, 11.2.

(1SR, 2SR, 3SR) Ethyl 2-(2-phenylethylcarbonyl)-3-methyl cyclopropyl-1-carboxylate Hexane/Ethyl acetate, 18:1. IR (film) 2980, 1728, 1702, 1371, 1186 cm$^{-1}$. H NMR (CDCl$_3$) 7.30-7.10 (m, 5H), 4.09 (c, J=7.0 Hz, 2H), 2.90 (s, 4H), 2.41 (m, 1H), 2.12 (m, 1H), 1.66 (m, 1H) , 1.10 (m, 6H). C NMR (CDCl$_3$) 206.8, 170.2, 140.8 128.5, 128.3, 126.2, 60.8, 45.5, 35.7, 30.1, 29.9, 25.9, 14.3, 11.3

(1SR, 2SR, 3SR) Ethyl 2-(2-phenylethylcarbonyl)-3-(phenylethyl) cyclopropyl) carboxylate Obtained using toluene as solvent. Hexane/Ethyl acetate, 12:1. IR (film) 1728, 1701, 1454, 1196, 1165, 700 cm$^{-1}$. H NMR (CDCl$_3$) 7.45- 7.15 (m, 10H), 4.10 (c, J=7.2 Hz, 2H), 2.90-2.60 (m, 8H), 2.23 (m, 1H), 1.85 (m, 1H), 1.70 (m, 1H), 1.25 (t, J=7.2 Hz, 3H). C NMR (CDCl$_3$) 206.7, 170.2, 140.9, 140.6, 128.5, 128.4, 128.3, 128.2, 126.0, 125.9, 60.6, 45.2, 35.3, 34.8, 31.1, 29.5, 28.9, 27.6.

(1SR, 2SR, 3SR) Ethyl 2-(2-phenylethylcarbonyl)-3-pentyl cyclopropyl-1-carboxylate Hexane/Ethyl acetate, 20:1. H NMR (CDCl$_3$) 7.40-7.10 (m, 5H), 4.16 (c, J=6.7 Hz, 2H), 2.91 (s, 4H), 2.50-2.30 (m, 2H), 1.80-1.65 (m, 1H), 1.65-1.50 (m, 1H), 1.30 (m, 7H), 0.86 (t, J=6.7 Hz, 3H). C NMR (CDCl$_3$) 206.6, 170.2, 140.7, 126.4, 126.2, 126.0, 60.70, 45.3, 34.7, 32.3, 31.9, 31.2, 29.6, 29.5, 25.6, 22.4, 14.1, 13.9.

(1SR, 2SR, 3SR) Ethyl 2-(2-phenylethylcarbonyl)-3-nonyl cyclopropyl-1-carboxylate Hexane/Ethyl acetate, 12:1. IR (film) 2926, 1730, 1701, 1454, 1184 cm$^{-1}$. H NMR (CDCl$_3$) 7.40-7.20 (m, 5H), 4.16 (q, J=7.1 Hz, 2H), 2.90 (s, 4H), 2.49-2.35 (m, 2H), 1.70-1.60 (m, 1H), 1.26 (m, 19H), 0.88 (t, J=6.2 Hz, 3H). C NMR (CDCl$_3$) 206.9, 170.3, 140.7, 128.5, 128.3, 126.1, 60.8, 45.4, 34.8, 32.0, 29.7 (2C), 29.5 (2C), 29.2, 29.1, 26.0, 22.6, 14.2, 14.1.

(1RS, 2SR, 3SR) Ethyl 2-(2-phenylethylcarbonyl)-3-nonyl cyclopropyl-1-carboxylate Hexane/Ethyl acetate, 12:1. IR (film) 2926, 1732, 1456, 1373, 1188 cm$^{-1}$. H NMR (CDCl$_3$) 7.60-7.15 (m, 5H), 4.09 (q, J=7.1 Hz, 2H), 2.88 (m, 4H), 2.15-1.85 (m, 3H), 1.25 (m, 19H), 0.88 (t, J=6.1 Hz, 3H). C NMR (CDCl$_3$) 204.9, 169.8, 141.0, 128.4, 128.3, 126.0, 60.8, 45.0, 35.3, 32.0, 31.8, 30.3, 29.6, 29.4 (2C), 29.2, 29.1, 28.6, 26.8, 22.6, 14.1, 14.0.

(1SR, 2SR, 3SR) Ethyl 2-(9-xanthylmethylcarbonyl)-3-methyl cyclopropyl-1-carboxylate Hexane/Ethyl acetate, 18:1. H NMR (CDCl$_3$) 7.40-7.00 (m, 8H), 4.56 (t, J=6.5 Hz, 1H), 4.10 (c, J=7.0 Hz, 2H), 2.86 (m, 2H), 2.60 (m, 2H), 1.70 (m, 1H), 1.22 (t, J=7.0 Hz, 3H), 1.10 (d, J=6.5Hz, 3H). C NMR (CDCl$_3$) 205.6, 169.7, 152.12, 152.10, 128.5, 127.8, 124.8, 123.4, 123.3, 116.5, 60.7, 54.5, 36.4, 34.8, 30.2, 26.1, 14.2, 11.1

(1SR, 2SR, 3SR) Ethyl 2-(9-xanthylmethylcarbonyl)-3-ethyl cyclopropy-1-carboxylate Hexane/Ethyl acetate, 9:1. IR (film) 2900, 1728, 1699, 1470, 1256, 1184 cm$^{-1}$. H NMR (CDCl$_3$) 7.30-7.00 (m, 8H), 4.58 (t, J=6.7 Hz, 1H), 4.10 (q, J=7.1 Hz, 2H), 2.94 (d, J=6.7 Hz, 2H), 2.28 (dd, J=4.6 and 9.3 Hz, 1H), 2.15 (t, J=4.6 Hz 1H), 1.70-1.40 (m, 3H), 1.23 (t, J=7.2 Hz, 3H), 0.81 (t, J=6.3 Hz, 3H). C NMR (CDCl$_3$) 206.9, 169.9, 152.1, 128.5 (2C), 128.4, 127.9, 124.9, 124.8, 123.4, 116.5, 60.8, 54.4, 35.7, 34.7, 33.7, 29.6, 19.4, 14.2, 13.4.

(1SR, 2SR, 3SR) Ethyl 2-(9-xanthylmethylcarbonyl)-3-propyl cyclopropyl-1-carboxylate Hexane/Ethyl acetate, 9:1. IR (KBr) 1721, 1689, 1458, 1254, 1184 cm$^{-1}$. H NMR (CDCl$_3$) 7.35-6.95 (m, 8H), 4.58 (t, J=6.5 Hz, 1H), 4.08 (q, J=7.1 Hz, 2H), 2.94 (d, J=6.5 Hz, 2H), 2.27 (dd, J=4.5 and 9.4 Hz, 1H), 2.15 (t, J=4.5 Hz 1H), 1.65 (m, 1H), 1.44 (m, 2H), 1.23 (m, 5H), 0.80 (t, J=6.4 Hz, 3H). C NMR (CDCl$_3$) 205.7, 170.0, 152.1, 128.5, 128.4, 127.9, 124.9, 124.8, 123.4, 116.5, 60.7, 54.4, 35.6, 34.7, 31.9, 29.5, 27.8, 22.3, 14.2, 13.5.

(1SR, 2SR, 3SR) Ethyl 2-(9-xanthylmethylcarbonyl)-3-butyl cyclopropyl-1-carboxylate Hexane/Ethyl acetate, 18:1. H NMR (CDCl$_3$) 7.35-6.95 (m, 8H), 4.57 (t, J=6.6 Hz, 1H), 4.09 (q, J=7.1 Hz, 2H), 3.00 (d, J=6.6 Hz, 2H), 2.29 (dd, J=4.6 and 9.4 Hz, 1H), 2.16 (t, J=5.7 Hz, 1H), 1.70 (m, 1H), 1.22 (m, 9H), 0.82 (t, J=6.4 Hz, 3H). C NMR (CDCl$_3$) 205.5, 169.7, 151.9, 128.4, 127.7, 124.7, 124.6, 123.2, 116.4, 60.6, 54.3, 35.6, 34.5, 32.0, 31.1, 29.4, 25.4, 21.9, 14.1, 13.8.

(1SR, 2SR, 3SR) Ethyl 2-(9-xanthylmethylcarbonyl)-3-pentyl cyclopropyl-1-carboxylate Hexane/Ethyl acetate, 12:1. IR (KBr) 2926, 1728, 1688, 1479, 1252 cm$^{-1}$. H NMR (CDCl$_3$) 7.40–7.05 (m, 8H), 4.59 (t, J=6.6 Hz, 1H), 4.09 (q, J=7.1 Hz, 2H), 2.94 (d, J=6.6 Hz, 2H), 2.29 (dd, J=4.6 and 9.4 Hz, 1H), 2.17 (dd, J=4.6 and 5.7 Hz, 1H), 1.70 (m, 1H), 1.24 (m, 11H), 0.84 (t, J=6.4 Hz, 3H). C NMR (CDCl$_3$) 205.6, 169.9, 152.1, 128.5, 127.8, 124.8, 123.4, 116.5, 60.7, 54.4, 35.7, 34.7, 32.2, 31.5, 29.6, 28.8, 25.8, 22.6, 14.2, 14.1.

(1SR, 2SR, 3SR) Ethyl 2-(9-xanthylmethylcarbonyl)-3-hexyl cyclopropyl-1-carboxylate Hexane/Ethyl acetate, 9:1. H NMR (CDCl$_3$) 7.45-6.90 (m, 8H), 4.58 (t, J=6.7 Hz, 1H), 4.03 (q, J=7.1 Hz, 2H), 2.94 (d, J=6.7 Hz, 2H), 2.30 (dd, J=4.6 and 9.4 Hz, 1H), 2.20 (dd, J=5.7 Hz, 1H), 1.70 (m, 1H) 1.23 (m, 13H), 0.84 (t, J=6.6 Hz, 3H). C NMR (CDCl$_3$) 205.7, 169.9, 152.1, 128.5, 128.4, 127.6, 124.7, 123.3, 116.5, 60.7, 54.4, 35.7, 34.7, 32.2, 31.6, 29.6, 29.0, 28.7, 25.8, 22.5, 14.2, 14.0.

(1SR, 2SR, 3SR) Ethyl 2-(9-xanthylmethylcarbonyl)-3-nonyl cyclopropyl-1-carboxylate Hexane/Ethyl acetate, 18:1. H NMR (CDCl$_3$) 7.30-6.95 (m, 8H), 4.56 (t, J=6.6 Hz, 1H), 4.09 (q, J=7.1 Hz, 2H), 2.94 (d, J=6.6 Hz, 2H), 2.29 (dd, J=4.6 and 9.4 Hz, 1H), 2.16 (dd, J=4.6 and 5.7 Hz, 1H), 1.70 (m, 1H), 1.24 (m, 19H), 0.87 (t, J=6.9 Hz, 3H). C NMR (CDCl$_3$) 205.7, 169.9, 152.1, 128.5, 128.4, 127.8, 124.8, 124.7, 123.3, 116.5, 60.7, 54.4, 35.6, 34.6, 32.2, 31.8, 29.5 (2C), 29.2, 29.1, 28.9, 25.8, 22.6, 14.1, 14.0.

(1SR, 2SR, 3SR) Ethyl 2-(9-xanthylmethylcarbonyl)-3-phenethyl cyclopropyl-1-carboxylate Hexane/Ethyl acetate, 9:1. IR (film) 1790, 1701, 1470, 1460,1253 cm$^{-1}$. H NMR (CDCl$_3$) 7.35-6.95 (m, 8H), 4.55 (t, J=6.5 Hz, 1H), 4.08 (q, J=7.0 Hz, 2H), 2.90-2.70 (m, 4H), 2.20 (m, 1H), 2.04 (t, J=5.7 Hz, 1H), 1.80-1.60 (m, 3H), 1.23 (m, 3H). C NMR (CDCl$_3$) 205.5, 169.9, 152.1, 140.9, 128.6, 128.5, 128.4, 127.9, 125.9, 124.9, 123.3, 116.5, 60.9, 54.4, 35.6, 35.3, 34.4, 29.1, 27.5, 14.2.

(1SR, 2SR, 3SR) Ethyl 2-(9-xanthylmethylcarbonyl)-3-isobutyl cyclopropyl-1-carboxylate Hexane/Ethyl acetate, 18:1. IR (KBr) 1728, 1690, 1477, 1252, 1184 cm$^{-1}$. H NMR (CDCl$_3$) 7.45-6.95 (m, 8H), 4.59 (t, J=6.7 Hz, 1H), 4.08 (q, J=7.0 Hz, 2H), 2.95 (d, J=6.7 Hz, 2H), 2.33-2.20 (m, 2H), 1.70 (m, 1H), 1.60 (m, 2H), 1.23 (t, J=7.1 Hz, 3H), 0.80 (t, J=6.1 Hz, 6H). C NMR (CDCl$_3$) 205.7, 169.9, 152.1, 128.4, 127.8, 124.8, 123.3, 116.5, 60.7, 54.5, 35.6, 34.6 (2C), 31.0, 29.5, 22.1, 22.0, 14.1 (2C).

4) Bucherer Berg reaction A solution of the ester (1 mmol) was dissolved in ethanol and then 1N NaOH (1.1 equiv) was added. The amount of ethanol used is the volume needed to run the reaction at 0.3M. The resuting solution was heated at 60_C until no starting material remains (TLC monitoring). After cooling the reaction mixture was extracted with ether and acidified with 1N HCl (in an ice bath). The acid was extracted with ether (or ethyl acetate) twice. The organic layer was dried over Na$_2$SO$_4$ and evaporated to yield a crude which was subjected to the Bucherer-Berg reaction without any further purification.

Method A

A solution of the ketone-acid (7.34 mmol) in ethanol (10 mL) was added to a solution of KCN (5 equiv.) and (NH$_4$)$_2$CO$_3$ (7 equiv.) in water (10 mL), then this mixture was heated to 60_C for 24 hours. The mixture was cooled in an ice bath and 10% KHSO4 was cautiously added till acidic pH. The mixture of hydantoines precipitate or are extracted with ethyl acetate.

Method B

The same as before but in a sealed tube in an oven at 100_C 6 hours.

(1SR, 2SR, 3SR) 5-Methyl-5-(2-ethoxycarbonyl-3-methyl cyclopropyl) pirazolidin-2,4-dione Method A. Diastereomer mixture at C-5, H NMR (DMSO-d$_6$) Diastereomer mixture at C-5, H NMR (DMSO-d$_6$) 7.82 (broad s, 2H), 4.15 (m, 2H), 1.80 (m, 1H), 1.50 (m, 1H), 1.40-1.00 (m, 10H). C NMR (DMSO-d$_6$) 77.5, 170.6, 156.3, 60.5, 60.2, 32.8, 22.6, 20.5, 17.9, 4.2, 11.5.

(1SR, 2SR, 3SR) 5-Phenylethyl-5-(2-ethoxycarbonyl-3-methyl cyclopropyl) pirazolidin-2,4-dione Method A. Diastereomer mixture at C-5, H NMR (DMSO-d$_6$) 8.10 (broad s, 1H), 7.90 (broad s, 1H), 4.10 (m, 2H), 3.00-1.30 (m, 7H), 1.10 (m, 6H). C NMR (DMSO-d$_6$) 175.9, 169.9, 169.8, 256.0, 140.1, 140.0, 127.8, 127.6, 127.5, 127.4, 125.4, 125.2, 63.2, 62.9, 59.7, 59.5, 43.4, 31.7, 31.3, 28.6, 28.5, 28.1, 24.1, 20.5, 19.2, 17.4, 15.9, 13.5, 10.7, 10.4.

(1SR, 2SR, 3SR) 5-Phenylethyl-5-(2-carboxy-3-phenylethyl cyclopropyl) pirazolidin-2,4-dione Method A. Diastereomer mixture at C-5, H NMR (DMSO-d$_6$) 8.10 (broad s, 2H), 7.90 (broad s, 1H), 7.40-7.10 (m, 5H), 2.70-1.10 (m, 11H). C NMR (DMSO-d$_6$) 177.1, 176.6, 172.9, 172.7, 158.9, 158.8, 141.7, 141.6, 140.8, 128.5, 128.3, 128.2, 128.1, 126.0, 125.7, 64.0, 63.9, 37.9, 35.1, 34.9, 31.3, 29.3, 28.3, 22.9.

(1SR, 2SR, 3SR) 5-Phenylethyl-5-(2-carboxy-3-pentyl cyclopropyl) pirazolidin-2,4-dione Method A. Diastereomer mixture at C-5, H NMR (DMSO-d$_6$) 7.90 (broad s, 2H), 7.80 (broad s, 1H), 7.40-7.10 (m, 5H), 3.70 (broad s, 1H), 3.00-2.80 (m, 1H), 2.70-2.40 (m, 2H), 2.10-1.70 (m, 2H), 1.60–1.20 (m, 10H), 0.86 (m, 3H). C NMR (DMSO-d$_6$) 176.6, 176.5, 172.4, 172.2, 156.7, 140.7, 127.9, 126.3, 126.2, 126.1,(2C), 125.9, 125.7, 63.8, 63.7, 30.7, 29.2, 28.4, 28.3, 28.2, 25.6, 25.3, 23.5, 22.0, 21.8, 21.7, 19.8, 13.7.

(1SR, 2SR, 3SR) 5-Phenylethyl-5-(2-carboxy-3-nonyl cyclopropyl) pirazolidin-2,4-dione Method A. Diastereomer mixture at C-5, H NMR (DMSO-d$_6$) 8.10 (broad s, 1H), 7.90 (broad s, 1H), 7.40-7.10 (m, 5H), 3.70 (broad s, 1H), 2.90–2.60 (m, 2H), 2.10-1.80 (m, 2H), 1.60-1.30 (m, 19H), 0.87 (t, J=6.5 Hz, 3H). C NMR (DMSO-d$_6$) 176.6, 172.5, 156.8, 140.8, 128.5, 128.3, 125.7, 63.9, 63.8, 31.0, 30.5, 29.3, 29.2, 29.0, 28.7, 25.7, 22.2, 19.9, 14.0.

(1RS, 2SR, 3SR) 5-Phenylethyl-5-(2-carboxy-3-nonyl cyclopropyl) pirazolidin-2,4-dione Method B (24 h). Diastereomer mixture at C-5, H NMR (DMSO-d$_6$) 8.10 (broad s, 1H), 8.00 (broad s, 1H), 7.30-7.00 (m, 5H), 3.50 (broad s, 1H), 2.50 (m, 2H), 2.00 (m, 2H), 1.50-1.30 (m, 19H), 0.87 (t, J=6.5 Hz, 3H). C NMR (DMSO-d$_6$) 177.4, 174.5, 157.0, 156.3, 140.8, 128.5, 126.2, 126.0, 63.6, 63.5, 29.8, 29.0, 22.1, 14.0.

(1SR, 2SR, 3SR) 5-(9-Xanthylmethyl)-5-(2 -carboxy-3-methyl cyclopropyl) pirazolidin-2,4-dione Method B. Diastereomer mixture at C-5, H NMR (DMSO-d$_6$) 7.90 (broad s, 2H), 7.40–6.90 (m, 8H), 4.60 (m, 1H), 2.50-0.80 (m, 8H). C NMR (DMSO-d$_6$) 175.8, 172.2, 156.6, 152.4, 128.4, 128.3, 128.1, 127.7, 127.1, 125.7, 123.6, 123.5, 116.3, 63.1, 45.0, 35.8, 34.4, 34.1, 30.7, 21.2, 20.2, 17.5, 16.4, 11.5, 11.1.

(1SR, 2SR, 3SR) 5-(9-Xanthylmethyl)-5-(2-carboxy-3-methyl cyclopropyl) pirazolidin-2,4-dione Method B. Diastereomer mixture at C-5, H NMR (DMSO-d$_6$) 7.90 (broad s, 2H), 7.40–6.90 (m, 8H), 4.60 (m, 1H), 2.50-0.80 (m, 8H). C NMR (DMSO-d$_6$) 175.8, 172.2, 156.6, 152.4, 128.4, 128.3, 128.1, 127.7, 127.1, 125.7, 123.6, 123.5, 116.3, 63.1, 45.0, 35.8, 34.4, 34.1, 30.7, 21.2, 20.2, 17.5, 16.4, 11.5, 11.1.

(1SR, 2SR, 3SR) 5-(9-Xanthylmethyl)-5-(2-carboxy-3-ethyl cyclopropyl) pirazolidin-2,4-dione Method B. Diastereomer mixture at C-5, H NMR (DMSO-d$_6$) 10.5 (broad s, 1H), 7.90 (broad s, 2H), 7.40-7.05 (m, 8H), 4.05 (in, 1H), 3.00 (in, 1H) 2.15 (m, 8H), 1.85 (m, 1H), 1.60-1.20 (m, 4H), 0. 80 (M, 3H). C NMR (DMSO-d$_6$)176.3, 175.9, 156.6, 152.4, 152.3, 151.4, 128.1, 127.9, 127.7, 127.3, 127.2, 125.6, 123.7, 123.4, 116.2, 63.1, 63.0, 40.3, 35.7, 32.9, 19.2, 18.8, 13.7, 13.5.

(1SR, 2SR, 3SR) 5-(9-Xanthylmethyl)-5-(2-carboxy-3-propyl cyclopropyl) pirazolidin-2,4-dione Method B. Diastereomer mixture at C-5, H NMR (DMSO-d$_6$) 7.90 (broad s, 2H), 7.40-6.90 (m, 8H), 4.50 (m, 1H), 2.10 (m, 1H), 1.90 (m, 1H), 1.70 (m, 1H), 1.25 (m, 6H), 0.85 (t, J=6.4 Hz, 3H). C NMR (DMSO-d$_6$) 176.5, 175.8, 172.4, 172.1, 128.7, 128.3, 128.2, 127.0, 125.6, 123.8, 116.3, 116.1, 63.0, 62.9, 35.7, 33.2, 27.6, 27.4, 23.1, 22.0, 21.8, 20.1, 13.5.

(1SR, 2SR, 3SR) 5-(9-Xanthylmethyl)-5-(2-carboxy-3-butyl cyclopropyl) pirazolidin-2,4-dione Method B. Diastereomer mixture at C-5, H NMR (DMSO-d$_6$) 7.95 (broad s, 1H), 7.85 (broad s, 1H), 7.20-6.90 (m, 8H), 4.00 (m, 1H), 2.15 (m, 1H), 1.80-1.60 (m, 2H)1.25(m, 8H), 0.75 (t, J=6.4 Hz, 3H). C NMR (DMSO-d$_6$) 176.0, 172.4, 156.6, 152.4, 151.5, 128.3, 128.2, 128.1, 127.8, 127.0, 125.8, 123.5, 116.3, 63.0, 62.8, 45.1, 35.7, 33.3, 31.0, 30.9, 25.3, 23.4, 21.6, 19.9, 13.8.

(1SR, 2SR, 3SR) 5-(9-Xanthylmethyl)-5-(2-carboxy-3-pentyl cyclopropyl) pirazolidin-2,4-dione Method B. Diastereomer mixture at C-5, H NMR (DMSO-d$_6$) 8.00 (broad s, 1H), 7.80 (broad s, 1H), 7.40-6.90 (m, 8H), 4.55 (m, 1H), 2.40 (m, 1H) 1.90 (m, 1H), 1.50-1.00 (m, 1H), 0.80 (m, 3H). C NMR (DMSO)-d$_6$) 175.9, 172.2, 156.6, 152.4, 151.5, 128.7, 128.2, 127.9, 127.8, 127.0, 125.6, 123.8, 116.3, 63.0, 40.7, 35.7, 26.3, 25.5, 23.4, 22.1, 22.0, 21.4, 13.9.

(1SR, 2SR, 3SR) 5-(9-Xanthylmethyl)-5-(2-carboxy-3-hexyl cyclopropyl) pirazolidin-2,4-dione Method B. Diastereomer mixture at C-5, H NMR (DMSO-d$_6$) 10.70 (broad s, 17H), 7.95 (broad s, 1H), 7.80 (broad s, 1H), 7.35-6.95 (m, 8H), 4.00 (m, 1H), 2.25 (m, 1H) 1.70 (m, 1H), 1.25 (m, 13H), 0.85 (t, J=6.4 Hz, 3H). C NMR (DMSO-d$_6$) 175.8, 172.0, 156.5, 152.3, 128.2, 128.0, 127.8, 127.0, 123.7, 116.3, 63.0, 40.7, 35.7, 33.3, 31.2, 28.7, 28.1, 25.5, 23.5, 22.0, 19.8, 13.9.

(1SR, 2SR, 3SR) 5-(9-Xanthylmethyl)-5-(2-carboxy-3-nonyl cyclopropyl) pirazolidin-2,4-dione Method B. Diastereomer mixture at C-5, H NMR (DMSQ-d$_6$) 8.00 (broad s, 1H), 7.90 (broad s, 1H), 7.40-6.90 (m, 8H), 4.00 (m, 1H), 3.20 (m, 1H) 2.40 (m, 1H), 1.70 (m, 1H), 1.20 (m, 18H), 0.85 (t, J=6.4 Hz, 3H). C NMR (DMSO-d$_6$) 175.8, 175.9, 172.4, 172.1, 156.6, 152.4, 152.3, 128.3, 128.2, 128.0, 127.9, 125.6, 125.5, 123.8, 116.3, 63.0, 62.7, 35.7, 33.6, 31.3, 29.0, 28.9, 28.7, 28.6, 28.5, 25.6, 23.5, 22.1, 19.8, 14.0.

(1SR, 2SR, 3SR) 5-(9-Xanthylmethyl)-5-(2-carboxy-3-phenylethyl cyclopropyl) pirazolidin-2,4-dione Method B. Diastereomer mixture at C-5, H NMR (DMSO-d$_6$) 8.00 (broad s, 1H), 7.80 (broad s, 1H), 7.30-7.00 (m, 13H), 4.00 (m, 1H), 2.20 (m, 2H) 1.90-1.30 (m, 7H). C NMR (DMSO-d$_6$) 176.0, 175.6, 172.4, 172.1, 156.6, 156.5, 152.5, 141.3, 141.2, 128.3, 128.2, 127.7, 125.7, 124.7, 123.6, 116.3, 116.0, 63.0, 62.9, 40.7, 35.7, 34.8, 33.7, 27.8, 23.2, 19.7.

(1SR, 2SR, 3SR) 5-(9-Xanthylmethyl)-5-(2-carboxy-3-isobutyl cyclopropyl) pirazolidin-2,4-dione Method B. Diastereomer mixture at C-5, H NMR (DMSO-d$_6$) 10.70 (broad s, 1H), 8.15 (broad s, 1H), 7.90 (broad s, 1H), 7.40-6.90 (m, 8H), 4.50 (m, 1H), 3.20 (m, 1H) 2.10 (m, 1H), 2.00 (m, 1H), 1.50-1.00 (m, 5H), 0.85 (d, J=6.4 Hz, 6H). C NMR (DMSO-d$_6$) 176.0, 175.8, 172.4, 172.2, 156.6, 152.5, 152.3, 129.0, 128.7, 127.9, 126.2, 125.5, 123.5, 116.3, 116.0, 63.1, 62.9, 45.1, 34.6, 34.3, 33.6, 33.2, 27.9, 27.8, 22.5, 22.0, 21.8, 20.9, 20.7, 19.9.

5) Basic hydrolysis

The mixture of hydantoines was treated with 1N NaOH at 150_C during 24 hours. After cooling the reaction mixture 12N HCl was added till pH=1–2 in an ice bath. Solvent evaporation yield a solid that was triturated with acetone several times in order to remove water. The resultant solid was chromatographied with Dowex resin and eluted with 10% Py or by adding water to the chloride salt the zwitterion precipitated.

(1SR, 2SR, 3SR) 3-Methyl-a-methyl-2-carboxycyclopropyl glycine

Dowex, MS (FAB) Calculated mass for C$_8$H$_{14}$NO$_4$ (M$^+$+ 1) 188.0923, found, 188.0922. Diasteromer mixture at the aminoacid center. H NMR (D$_2$O/Py-d$_5$) 1.80 (m, 1H), 1.60-1.40 (m, 5H), 1.13 (d, J=6.0 Hz, 3H). C NMR (D$_2$O/ Py-d$_5$) 178.6, 174.7, 61.1, 31.4, 26.8, 20.6, 18.7, 17.8, 17.4, 11.7, 11.6.

(1SR, 2SR, 3SR) 3 -Methyl-a-phenylethyl-1-carboxycyclopropyl glycine

Dowex, Diasteromer mixture at the aminoacid center. IR (KBr) 3028, 2359, 1614, 1384, 696 cm$^{-1}$. H NMR (D$_2$O/ KOD) 7.50-7.20 (m, 5H), 2.70 (m, 1H), 2-50 (m, 1H), 2.10 (m, 1H), 1.80-1.50 (m, 2H), 1.40 (m, 1H), 1.20 (m, 1H), 1.10 (m, 3 H). C NMR (D$_2$O/KOD) 185.0, 184.0, 145.6, 131.4, 131.2, 128.7, 63.1, 44.7, 43.5, 37.8, 37.6, 33.2, 28.0, 19.8, 18.9, 14.9, 14.7.

(1SR, 2SR, 3SR) 3-Phenylethyl-a-phenylethyl-2-carboxycyclopropyl glycine

Dowex. Diasteromer mixture at the aminoacid center. H NMR (D$_2$O/Py-d$_5$) 7.10-6.80 (m, 10H), 2.50-2.20 (m, 4H), 1.80-1.40 (m, 3H). C NMR (D$_2$O/Py-d$_5$) 178.4, 173.4, 141.9, 140.4, 128.38, 128.28, 128.09, 127.9, 126.1, 125.5, 64.3, 35.8, 34.3, 30.7, 29.3, 28.6, 26.2, 24.8, 23.4.

(1SR, 2SR, 3SR) 3-Pentyl-a-phenylethyl-2-carboxycyclopropyl glycine

Dowex. Diasteromer mixture at the aminoacid center. H NMR (D$_2$O/KOD) 7.40-7.00 (m, 5H), 2.70-2.40 (m, 2H), 2.20-1.90 (m, 2H), 1.80-1.10 (m, 11H), 1.00-0.70 (m, 3H). C NMR (D$_2$O/KOD) 183.7, 182.8, 182.0, 181.9, 144.1, 143.7, 129.8, 129.6, 129.5, 127.0, 126.9, 61.9, 60.8, 44.3, 42.7, 35.7, 35.3, 32.2, 31.6, 30.2, 29.8, 28.3, 28.1, 26.8, 25.1, 24.0, 23.5, 23.3, 14.8, 14.7.

(1SR, 2SR, 3SR) 3-Nonyl-a-phenylethyl-2-carboxycyclopropyl glycine

Dowex, Diasteromer mixture at the aminoacid center. H NMR (MeOH-d4) 7.20 (m, 5H), 2.80-2.50 (m, 2H), 2.30-1.70 (m, 2H), 1.40 (m, 19H), 0.90 (t, J=6.5 Hz, 3H). C NMR (D$_2$O/Py-d$_5$) 178.3, 174.2, 140.6, 128.3, 128.2, 125.6, 124.5, 122.4, 64.1, 60.2, 36.8, 31.0, 30.9, 29.7, 28.9, 28.8, 28.9, 28.4, 27.0, 24.8, 23.9, 21.9, 13.4.

(1RS, 2SR, 3SR) 3-Nonyl-a-phenylethyl-2-carboxycyclopropyl glycine

Dowex, Diasteromer mixture at the aminoacid center. H NMR (D$_2$O/KOD) 7.30-7.00 (m, 5H), 2.60 (m, 1H), 2.10 (m, 1H), 1.20 (m, 21H), 0.90 (m, 3H). C NMR (D$_2$O/Py-d$_5$) 179.2, 178.1, 173.3, 176.4, 140.5, 139.9, 128.4, 128.3, 126.1, 66.2, 31.8, 31.2, 29.5, 29.3, 28.9, 22.6, 14.1.

(1SR, 2SR, 3SR) 3-Methyl-a-9-xanthylmethyl-2-carboxycyclopropyl glycine

Dowex, Diasteromer mixture at the aminoacid center. H NMR (D$_2$O/KOD) 7.50-7.00 (m, 8H), 4.10 (m, 1H), 2.20 (m, 1H), 1.80-0.80 (m, 7H). C NMR (D$_2$O/KOD) 182.7, 181.6, 154.3, 129.7, 129.5, 129.2, 128.8, 128.4, 125.1, 125.0, 117.6, 117.3, 61.3, 61.2, 38.1, 37.6, 37.5, 26.3, 17.5, 13.3, 13.0.

(1SR, 2SR, 3SR) 3-Ethyl-a-9-xanthylmethyl-2-carboxycyclopropyl glycine

Dowex, Diasteromer mixture at the aminoacid center. H NMR (D$_2$O/Py-d$_5$) 7.40-6.70 (m, 8H), 4.00 (m, 1H), 2.40-1.10 (m, 7H), 0.8 (m, 3H). C NMR (D$_2$O/Py-d$_5$) 178.3, 172.5, 171.2, 152.7, 151.9, 128.5, 128.1, 127.8, 127.6, 126.3, 125.3, 116.9, 116.0, 64.4, 63.9, 44.9, 42.4, 36.4, 36.1, 32.0, 31.7, 26.6, 25.6, 25.1, 20.2, 12.7.

(1SR, 2SR, 3SR) 3-Propyl-a-9-xanthylmethyl-2-carboxycyclopropyl glycine

Dowex, Diasteromer mixture at the aminoacid center. H NMR (D$_2$O/KOD) 7.40-6.90 (m, 8H), 4.00 (m, 1H), 3.79 (m, 1H), 2.50-1.50 (m, 2H), 1.20 (m, 6H), 0.90 (m, 3H). C NMR (D$_2$O/KOD) 182.2, 180.7, 154.4, 153.8, 130.0, 129.7, 129.6, 129.2, 129.1, 128.8, 125.1, 117.7, 117.3, 6.2, 38.2, 34.3, 30.5, 26.4, 23.1, 20.9, 19.4, 14.4.

(1SR, 2SR, 3SR) 3-Butyl-a-9-xanthylmethyl-2-carboxycyclopropyl glycine

Water, Diasteromer mixture at the aminoacid center. H NMR (D$_2$O/KOD) ) 7.12-6.40 (m, 8H), 4.00 (m, 1H), 2.00 (m, 1H), 1.50-1.00 (m, 10H), 0.80 (m, 3H). C NMR (D$_2$O/KOD) 182.9, 182.0, 154.0, 153.5, 129.6, 129.3, 128.5, 124.9, 117.7, 117.3, 60.7, 60.1, 38.1, 36.5, 32.3, 32.1, 27.6, 23.3, 22.9, 14.6.

(1SR, 2SR, 3SR) 3-Pentyl-a-9-xanthylmethyl-2-carboxycyclopropyl glycine

Water, Diasteromer mixture at the aminoacid center. H NMR (D$_2$O/Py-d$_5$) 7.20-6.70 (m, 8H), 3.90 (m, 1H), 2.40-2.00 (m, 2H), 1.60-0.90 (m, 11H), 0.80 (m, 3H). C NMR (D$_2$O/Py-d$_5$) 179.3, 179.0, 159.3, 153.2, 129.8, 129.3, 129.2, 117.1, 65.4, 45.3, 36.7, 33.4, 31.6, 29.5, 27.2, 24.6, 23.6, 23.0, 14.4.

(1SR, 2SR, 3SR) 3-Hexyl-a-9-xanthylmethyl-2-carboxycyclopropyl glycine

Water, Diasteromer mixture at the aminoacid center. H NMR (D$_2$O/KOD) ) 7.30-6.80 (m, 8H), 4.00 (m, 1H), 2.20 (m, 1H), 1.40-0.70 (m, 17H). C NMR (D$_2$O/KOD) 184.0, 182.0, 153.5, 129.7, 129.1, 128.9, 128.5, 124.9, 117.6, 117.2, 60.7, 38.2, 32.5, 30.0, 29.8, 27.6, 24.0, 23.2, 14.8, 14.6.

(1SR, 2SR, 3SR) 3-Nonyl-a-9-xanthylmethyl-2-carboxycyclopropyl glycine

Water, Diasteromer mixture at the aminoacid center. H NMR (D$_2$O/KOD) 7.20-6.80 (m, 8H), 4.00 (m, 1H), 2.00-0.80 (m, 24H). C NMR (D$_2$O/KOD) 182.8, 181.8, 18.6, 153.5, 153.2, 129.5, 128.6, 127.6, 124.5, 117.1, 66.8, 60.5, 33.0, 30.6, 27.4, 23.9, 15.1

(1SR, 2SR, 3SR) 3-Phenylethyl-a-9-xanthylmethyl-2-carboxycyclopropyl glycine

Water, Diasteromer mixture at the aminoacid center. H NMR (D$_2$O/KOD) 7.40-6.80 (m, 13H), 4.00 (m, 1H), 2.50 (m, 1H), 2.20-0.90 (m, 8H). C NMR (D$_2$O/KOD) 182.8, 181.8, 11.6, 154.1, 154.0, 153.6, 143.6, 143.1, 129.6, 129.5, 126.7, 126.8, 124.9, 117.6, 117.3, 61.6, 60.8, 49.6, 48.1, 47.7, 38.3, 37.2, 36.0, 35.8.

(1SR, 2SR, 3SR) 3-isoButyl-a-9-xanthylmethyl-2-carboxycyclopropyl glycine

Water, Diasteromer mixture at the aminoacid center. H NMR (D$_2$O/KOD) 7.40-7.00 (m, 8H), 4.20 (m, 1H), 2.20 (m, 1H), 1.90-1.30 (m, 7H), 0.80 (d, J=6.4 Hz, 6H). C NMR (D$_2$O/KOD) 182.7, 182.4, 182.1, 181.8, 154.0, 153.5, 129.7, 129.4, 129.2, 129.1, 128.7, 128.3, 125.1, 117.6, 117.3, 61.3, 36.2, 27.1, 36.8, 26.5, 28.9, 25.7, 23.1, 23.0, 22.8, 22.4.

(2R,5S,1'R,2'R,3'R/2R,5S,1'S,2'S,3'S) -2,5-dihydro-2-isopropyl-5-(2'-ethoxycarbonyl 3'-alkylcyclopropyl)-3,6-dimethoxypyrazine General Procedure A solution of (2R)-(−)-2,5-dihydro-2-isopropyl-3,6-dimethoxypyrazine (1 mmol) in THF (1.5 mL) under a dry nitrogen atmosphere, was cooled to −78° C. A 1.6M solution of n-butyllithium in hexane (1.5 mmol) was injected slowly into the reaction mixture and stirring was continued at −78° C. for 30 min. Then the γ-bromo α,γ-unsaturated ester (1.5 mmol) dissolved in THF (1.5 mL) was injected into the solution at −78° C. and the mixture maintained at this temperature for 2–3 h and then was hydrolysed with water and extracted with dichlorometane (3×25 mL). The combined of organic layers were dried over magnesium sulphate anhydride and evaporated under reduced pressure to give a oil which was purified by chromatography (hex/AcOEt: 15/1) to give the following compounds:

(2R,5S,1'R,2'R,3'R)-2,5-dihydro-2-isopropyl-5-(2'-ethoxycarbonyl-3'-methyl cyclopropyl)-3,6-dimethoxypyrazine $[\alpha]_D$=−23.5 (c=0.68, CHCl$_3$); $^1$H-NMR (200 MHz. CDCl$_3$): 0.69 (d, J=6.8 Hz, 3H), 1.04 (d, J=6.8 Hz, 3H), 1.14 (m, 3H), 1.27 (t, J=7.2 Hz, 3H), 1.64 (m, 1H), 1.91 (m, 1H), 2.07 (m, 1H), 2.22 (dh, J=3.4, 6.8 Hz, 1H), 3.63 (s, 3H), 3.73 (s, 3H), 3.92 (t, J=3.7 Hz, 1H), 4.05 (t, J=3.7 Hz, 1H) and 4.16 ppm (q, J=7.2 Hz, 2H); $^{13}$C-RMN (50 MHz, CDCl$_3$): 11.45, 14.40, 16.71, 17.82, 18.98, 21.70, 30.16, 31.96, 52.46, 52.59, 53.25, 60.19, 60.80, 163.47, 164.76 and 172.59 ppm; IR (oil, ν): 1728 and 1695 cm$^{-1}$ (C=O and C=N).

(2R,5S,1'S,2'S,3'S)-2,5-dihydro-2-isopropyl-5-(2'-ethoxycarbonyl-3'-methyl cyclopropyl)-3,6-dimethoxypyrazine $[\alpha]_D$=+37.38 (c=1.95, CHCl$_3$); $^1$H-NMR (300 MHz. CDCl$_3$): 0.69 (d, J=7.1 Hz, 3H), 1.03 (d, J=7.1 Hz, 3H), 1.22 (d, J=7.0 Hz, 3H), 1.24 (t, J=7.2 Hz, 3H), 1.48 (dd, J=5.1, 9.2 Hz, 1H), 1.69 (m, 1H), 1.82 (m, 1H), 2.24 (m, 1H), 3.63 (s, 3H), 3.71 (s, 3H), 3.92 (t, J=3.6 Hz, 1H), 4.01 (dd, J=3.6, 4.4 Hz, 1H) and 4.11 ppm (q, J=7.2 Hz, 2H); $^{13}$C-RMN (50 MHz, CDCl$_3$): 11.46, 14.32, 16.64, 18.97, 19.09, 21.01, 30.89, 31.86, 52.41, 52.63, 53.73, 60.12, 60.70, 163.26, 169.69 and 172.31 ppm; IR (oil, ν): 1726, 1703 and 1693 cm$^{-1}$ (C=O and C=N).

(2R,5S,1'R,2'R,3'R)-2,5-dihydro-2-isopropyl-5-(2'-ethoxycarbonyl-3'-ethyl cyclopropyl)-3,6-dimethoxypyrazine $[\alpha]_D$=−17.62 (c=0.91, CHCl$_3$); $^1$H-NMR (200 MHz. CDCl$_3$): 0.68 (d, J=6.9 Hz, 3H), 0.86 (t, J=7.3 Hz, 3H), 1.03 (d, J=6.9 Hz, 3H), 1.27 (t, J=7.2 Hz, 3H), 1.5 (qt, J=7.4 Hz, 2H), 1.90 (dd, J=5.0, 11.4 Hz, 1H), 2.09 (dd, J=5.0, 9.1 Hz, 1H), 2.22 (dh, J=3.5, 6.9 Hz, 1H), 3.64 (s, 3H), 3.70 (s, 3H), 3.93 (t, J=3.5 Hz, 1H), 4.07 (t, J=4.3 Hz, 1H) and 4.15 ppm (q, J=7.2 Hz, 2H); $^{13}$C-RMN (50 MHz, CDCl$_3$): 13.56, 14.27, 16.56, 18.89, 19.41, 21.36, 25.31, 29.35, 31.67, 52.41, 53.20, 60.10, 60.68, 163.32, 164.67 and 172.56 ppm; IR (oil, v): 1728 and 1693 cm$^{-1}$ (C=O and C=N).

(2R, 5S,1'S, 2'S, 3'S)-2,5-dihydro-2-isopropyl-5-(2'-ethoxycarbonyl-3'-ethyl cyclopropyl)-3,6-dimethoxypyrazine $[\alpha]_D$=+37.10 (c=1.0, CHCl$_3$); $^1$H-NMR (200 MHz. CDCl$_3$): 0.68 (d, J=6.9 Hz, 3H), 0.92 (t, J=6.9 Hz, 3H), 1.04 (d, J=6.9 Hz, 3H), 1.25 (t, J=7.2 Hz, 3H), 1.53 (m, 4H), 1.84 (dd, J=5.0, 10.9 Hz, 1H), 2.25 (dh, J=3.4, 6.8 Hz, 1H), 3.64 (s, 3H), 3.71 (s, 3H), 3.93 (t, J=3.4 Hz, 1H), 3.98 (t, J=4.2 Hz, 1H) and 4.11 ppm (q, J=7.2 Hz, 2H); $^{13}$C-RMN (50 MHz, CDCl$_3$): 13.64, 14.21, 16.49, 18.92, 19.68, 20.77, 26.67, 32.20, 31.66, 52.33, 52.42, 54.22, 60.04, 60.54, 163.10, 164.50 and 172.29 ppm; IR (oil, v): 1726 and 1697 cm$^{-1}$ (C=O and C=N).

(2R,5S,1'R,2'R,3'R)-2,5-dihydro-2-isopropyl-5-(2'-ethoxycarbonyl-3'-propyl cyclopropyl)-3,6-dimethoxypyrazine $[\alpha]_D$=−5.29 (c=1.03, CHCl$_3$); $^1$H-NMR (200 MHz. CDCl$_3$): 0.69 (d, J=6.8 Hz, 3H), 0.86 (t, J=7.2 Hz, 3H), 1.03 (d, J=6.8 Hz, 3H), 1.45 (t, J=6.6 Hz, 3H), 1.2-1.5 (m, 4H), 1.92 (m, 1H), 2.08 (dd, J=4.8, 9.1 Hz, 1H), 2.23 (dh, J=3.4, 6.8 Hz, 1H), 3.64 (s, 3H), 3.72 (s, 3H), 3.93 (t, J=3.4 Hz, 1H), 4.07 (t, J=4.8 Hz, 1H) and 4.15 ppm (q, J=6.8 Hz, 2H); $^{13}$C-RMN (50 MHz, CDCl$_3$): 13.66, 14.32, 16.59, 18.93, 21.34, 22.47, 23.45, 28.11, 29.31, 31.90, 52.42, 53.28, 60.14, 60.69, 163.22, 164.67 and 172.64 ppm; IR (oil, v): 1728 and 1697 cm$^{-1}$ (C=O and C=N).

(2R,5S,1'S,2'S,3'S)-2,5-dihydro-2-isopropyl-5-(2'-ethoxycarbonyl-3'-propyl cyclopropyl)-3,6-dimethoxypyrazine $[\alpha]_D$=+36.38 (c=1.01, CHCl$_3$); $^1$H-NMR (200 MHz. CDCl$_3$): 0.66 (d, J=6.8 Hz, 3H), 0.91 (t, J=7.0 Hz, 3H), 1.06 (d, J=6.8 Hz, 3H), 1.24 (t, J=7.1 Hz, 3H), 1.2-1.7 (m, 6H), 1.83 (dd, J=4.9, 10.6 Hz, 1H), 2.24 (dh, J=3.1, 6.8 Hz, 1H), 3.54 (s, 3H), 3.77 (s, 3H), 3.90 (m, 2H) and 4.10 ppm (q, J=7.4 Hz, 1H); $^{13}$C-RMN (50 MHz, CDCl$_3$): 13.88, 14.24, 16.36, 16.53, 19.04, 20.83, 22.51, 24.95, 28.37, 30.14, 31.46, 52.28, 52.48, 57.75, 60.56, 161.32, 164.76 and 172.38 ppm; IR (oil, v): 1728 and 1699 cm$^{-1}$ (C=O and C=N).

2.-Synthesis of (2S,1'R,2'R,3'R/2S,1'S,2'S,3'S)-2-(2'-ethoxycarbonyl-3'-alkyl cyclopropyl)glycine General Procedure 0.1N HCl (2 mmol, 20 mL) was added to a solution of above dihydropyrazine (1 mmol) in THF (10 mL) and stirring continued for 24h at room temperature. The mixture was extracted with ether which was discarded. The water layer was saturated with sodium chloride, ether was added and the solution brought to pH 8–10 with concentrated ammonium. The ether layer was separated and the water layer extracted four times with ether. The combined ether layers were dried over sodium sulphate anhydride and evaporated under reduced pressure to give the desired compounds.

(2S,1'R,2'R,3'R)-2-(2'-ethoxycarbonyl-3'-methylcyclopropyl)glycine $[\alpha]_D$=+56.6 (c=1.1, CHCl$_3$); $^1$H-NMR (200 MHz. CDCl$_3$): 1.19 (d, J=6.0 Hz, 3H), 1.26 (t, J=7.0 Hz, 3H), 1.34 (m, 1H), 1.60 (dd, J=5.0, 13.1 Hz, 1H), 1.74 (br s, 2H), 1.83 (dd, J=5.0, 9.0 Hz, 1H), 3.22 (d, J=7.0 Hz, 1H), 3.74 (s, 3H) and 4.11 ppm (q, J=7.1 Hz, 2H); $^{13}$C-RMN (50 MHz, CDCl$_3$): 11.65, 14.27, 19.94, 23.29, 31.16, 52.14, 53.33, 60.34, 171.62 and 174.77 ppm; IR (oil, v): 3381, 3323 (NH) and 1732 cm$^{-1}$ (C=O).

(2S,1'S,2'S,3'S)-2-(2'-ethoxycarbonyl-3'-methylcyclopropyl)glycine $[\alpha]_D$=+26.9 (c=1.0, CHCl$_3$); $^1$H-NMR (200 MHz. CDCl$_3$): 1.19 (d, J=5.9 Hz, 3H), 1.27 (t, J=7.2 Hz, 3H), 1.40-1.7 (m, 5H), 3.10 (d, J=7.4 Hz, 1H), 3.76 (s, 3H) and 4.13 ppm (q, J=7.2 Hz, 2H); $^{13}$C-RMN (50 MHz, CDC$_3$): 11.41, 14.28, 20.83, 23.44, 31.91, 52.24, 56.11, 60.43, 171.66 and 174.76 ppm; IR (oil, v): 3383, 3325 (NH), 1724 and 1738 cm$^{-1}$ (C=O).

(2S,1'R,2'R,3'R)-2-(2'-ethoxycarbonyl-3'-ethylcyclopropyl)glycine $[\alpha]_D$=+20.27 (c=1.1, CHCl$_3$); $^1$H-NMR (200 MHz. CDCl$_3$): 0.92 (t, J=7.4 Hz, 3H), 1.26 (t, J=7.1 Hz, 3H), 1.53 (dd, J=5.8, 7.2 Hz, 1H), 1.66 (m, 1H), 1.71 (br s, 2H), 1.86 (dd, J=5.0, 9.2 Hz, 1H), 3.25 (d, J=6.8 Hz, 1H), 3.74 (s, 3H) and 4.13 ppm (q, J=7.1 Hz, 2H); $^{13}$C-RMN (50 MHz, CDCl$_3$): 13.55, 14.14, 19.53, 22.73, 27.28, 30.28, 52.02, 54.91, 60.25, 171.66 and 174.69 ppm; IR (oil, v): 3382, 3321 (NH), 1736 and 1724 cm$^{-1}$ (C=O)

2S,1'S,2'S,3'S)-2-(2'-ethoxycarbonyl-3'-thylcyclopropyl)glycine $[\alpha]_D$=+40.1 (c=1.0, CHCl$_3$); $^1$H-NMR (200 MHz. CDCl$_3$): 0.91 (t, J=7.2 Hz, 3H), 1.26 (t, J=7.2 Hz, 3H), 1.3-1.64 (m, 4H), 1.65 (br s, 2H), 1.75 (dd, J=3.9, 8.8 Hz, 1H), 3.04 (d, J=7.1 Hz, 1H), 3.75 (s, 3H) and 4.13 ppm (q, J=7.2 Hz, 2H); $^{13}$C-RMN (50 MHz, CDCl$_3$): 13.43, 14.16, 19.53, 23.34, 28.42, 31.32, 51.98, 56.46, 60.35, 171.63 and 174.68 ppm; IR (oil, v): 3383, 3319 (NH), 1736 and 1724 cm$^{-1}$ (C=O).

(2S, 1'R, 2'R, 3'R) -2-(2'-ethoxycarbonyl-3'-propylcyclopropyl)glycine $[\alpha]_D$+18.8 (c=1.0, CHCl$_3$); $^1$H-NMR (200 MHz. CDCl$_3$): 0.89 (t, J=7.0 Hz, 3H), 1.26 (t, J=7.1 Hz, 3H) , 1.2-1.7 (m, 6H), 1.86 (dd, J=4.9, 9.1 Hz, 1H), 2.85 (br s, 2H), 3.28 (d, J=7.0 Hz, 1H), 3.75 (s, 3H) and 4.15 ppm (q, J=7.1 Hz, 2H); $^{13}$C-RMN (50 MHz, CDCl$_3$): 13.68, 14.23, 22.53, 22.94, 25.61, 28.29, 29.97, 52.21, 55.04, 60.39, 171.75 and 174.45 ppm; IR (oil, v): 3377 (NH), 1738 and 1728 cm$^{-1}$ (C=O).

(2S,1'S,2'S,3S)-2-(2'-ethoxycarbonyl-3'-propylcyclopropyl)glycine $[\alpha]_D$=+29.19 (c=1.4, CHCl$_3$); $^1$H-NMR (200 MHz. CDCl$_3$): 0.90 (t, J=7.2 Hz, 3H), 1.26 (t, J=7.1 Hz, 3H), 1.3-2.0 (m, 9H), 3.05 (d, J=7.8 Hz, 1H), 3.75 (s, 3H) and 4.12 ppm (q, J=7.1 Hz, 2H); $^{13}$C-RMN (50 MHz, CDCl$_3$): 13.67, 14.19, 2.32, 23.32, 26.56, 28.22, 31.25, 52.03, 56.45, 60.39, 171.71 and 174.69 ppm; IR (oil, v): 3379, 3323 (NH), 1740 and 1728 cm$^{-1}$ (C=O).

Synthesis of (2S,1'R,2'R,3'R/2S,1'S,2'S,3'S)-2-(2'-carboxy-3,-alkyl cyclopropyl)glycine General procedure The (S)-α-aminoacid diester (1 mmol) is refluxed in 6N HCl (5 mL) for 2 h. the solvent is evaporated and the residual crude dissolved in absolute ethanol (5 mL). To this solution, methyloxirane (2 mL) is added, the mixture is refluxed for 15 min., and then cooled to 0° C. the precipitated product is isolated by suction (In some case it was found necessary to wash with ether in order to recover solid).

(2S,1'R,2'R,3'R)-2-(2'-carboxy-3'-methylcyclopropyl)glycine m.p.>150° C. (dec.); $[\alpha]_D$=−26.7 (c=0.42, H$_2$O); $^1$H-NMR (200 MHz. D$_2$O): 0.93 (d, J=5.5 Hz, 3H), 1.37 (m, 2H), 1.79 (dd, J=5.5, 9.0 Hz, 1H) and 3.15 ppm (d, J=9.0 Hz, 1H); $^{13}$C-RMN (50 MHz, D$_2$O): 11.15, 21.67, 25.41, 27.86, 57.01, 172.79 and 175.43 ppm; IR (KBr, v): 3600-2200 (CO$_2$H), 3431 (NH), 1697 and 1630 cm$^{-1}$ (C=O).

(2S,1'S,2'S,3'S)-2-(2'-carboxy-3'-methylcyclopropyl) glycine m.p.>151° C. (dec.); $[\alpha]_D$=+31.5 (c=0.25, $H_2O$); $^1$H-NMR (200 MHz. $D_2O$): 0.93 (d, J=5.8 Hz, 3H), 1.39 (m, 2H), 1.66 (dd, J=4.7, 9.5 Hz, 1H) and 3.03 ppm (d, J=9.5 Hz, 1H); $^{13}$C-RMN (50 MHz, $D_2O$): 11.16, 22.10, 25.32, 28.12, 57.66, 172.40 and 176.09 ppm; IR (KBr, v): 3600-2700 ($CO_2H$), 3437 (NH) and 1630 cm$^{-1}$ (C=O).

(2S,1'R,2'R,3'R)-2-(2'-carboxy-3'-ethylcyclopropyl)glycine m.p.>152° C. (dec.); $[\alpha]_D$=+24.4 (c=0.31, $H_2O$); $^1$H-NMR (200 MHz. $D_2O$): 0.67 (m, 3H), 1.31 (m, 4H), 1.76 (m, 1H) and 3.14 ppm (d, J=8.9 Hz, 1H); $^{13}$C-RMN (50 MHz, $D_2O$): 12.83, 19.89, 24.92, 26.89, 29.16, 56.95, 172.74 and 175.75 ppm; IR (KBr, v): 3600-2700 ($CO_2H$), 3429 (NH), 1697 and 1628 cm$^{-1}$ (C=O).

(2S,1'S,2'S,3'S)-2-(2'-carboxy-3'-ethylcyclopropyl)glycine m.p.>194° C. (dec.); $[\alpha]_D$=+37.98 (c=0.30, $H_2O$); $^1$H-NMR (200 MHz. $D_2O$): 0.67 (t, J=7.0 Hz, 3H), 1.35 (m, 4H), 1.69 (dd, J=7.0, 13.8 Hz, 1H) and 3.0 ppm (d, J=9.1 Hz, 1H); $^{13}$C-RMN (50 MHz, $D_2O$): 12.72, 19.82, 24.57, 27.66, 29.79, 57.54, 172.83 and 175.83 ppm; IR (KBr, v): 3700-2700 (CO2H), 3433 (NH), 1678 and 1616 cm$^{-1}$ (C=O).

(2S,1'R,2'R,3'R)-2-(2'-carboxy-3'-propylcyclopropyl) glycine m.p.>138° C. (dec.); $[\alpha]_D$=+28.39 (c=0.28, $H_2O$); $^1$H-NMR (200 MHz. $D_2O$): 0.63 (t, J=6.2 Hz, 3H), 1.0-1.5 (m, 6H), 1.74 (dd, J=5.1, 8.8 Hz, 1H) and 3.16 ppm (d, J=8.8 Hz, 1H); $^{13}$C-RMN (50 MHz, $D_2O$): 13.29, 21.99, 25.05, 26.73, 27.42, 28.51, 56.91, 172.99 and 176.15 ppm; IR (KBr, v): 3600-2300 ($CO_2H$), 3433 (NH), 1684 and 1630 cm$^{-1}$ (C=O).

(2S,1'S,2'S,3'S)-2-(2'-carboxy-3'-propylcyclopropyl)glycine m.p.>190° C. (dec.); $[\alpha]_D$=+41.04 (c=0.26, $H_2O$); $^1$H-NMR (200 MHz. $D_2O$): 0.68 (m, 3H), 1.29 (m, 6H), 1.67 (m, 1H) and 2.99 ppm (d, J=9.6 Hz, 1H); $^{13}$C-RMN (50 MHz, $D_2O$): 13.27, 21.87, 25.12, 27.43, 27.77, 28.44, 57.85, 173.28 and 176.65 ppm; IR (KBr, v): 3700-2300 ($CO_2H$), 3441 (NH), 1670 and 1628 cm$^{-1}$ (C=O).

Example 6

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Example 7

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |

-continued

| | |
|---|---|
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on tablet machine to yield tablets each weighing 150 mg.

EXAMPLE 8

Capsules each containing 80 mg medicament are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Example 9

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

What is claimed is:

1. A compound of the formula:

in which $R^1$ is $C_{1-10}$ alkyl, $C_{2-10}$ alkenyl, $C_{2-10}$ alkynyl, $C_{3-10}$ cycloalkyl, $C_{3-10}$ cycloalkyl-$C_{1-10}$ alkyl, $C_{3-10}$ cycloalkyl-$C_{2-10}$ alkenyl, $C_{3-10}$ cycloalky-$C_{2-10}$ alkynyl, optionally substituted phenyl-$C_{1-10}$ alkyl, optionally substituted phenyl-$C_{2-10}$ alkenyl, optionally substituted phenyl-$C_{2-10}$ alkynyl, optionally substituted naphthyl, optionally substituted naphthyl-$C_{1-10}$ alkyl, $C_{1-10}$ alkoxy-$C_{1-10}$ alkyl, $C_{3-10}$ cycloalkoxy-$C_{1-10}$ alkyl, optionally substituted heterocyclyl, optionally substituted heterocyclyl-$C_{1-10}$ alkyl, optionally substituted phenyl fused to $C_{5-10}$ cycloalkyl, optionally substituted tricyclic, optionally substituted tricyclic-$C_{1-10}$ alkyl, or (optionally substituted phenyl$(CH_2)_n)_2$ $C_{1-10}$ alkyl, where n is 0 or 1 to 4, and $R^2$ is hydrogen or one of the values for $R^1$; provided that when $R^2$ is hydrogen, $R^1$ is not methoxymethyl; or a salt or ester thereof.

2. A compound according to claim 1 in which $R^2$ is H.

3. A compound according to claim 1 in which the tricyclic group is of the formula

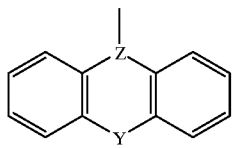

where Z is

or

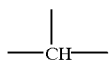

and Y is —O—, —S—, —SO—, —$SO_2$—, —CH=CH—, —$(CH_2)_p$— where p is 1, 2 or 3.

4. A compound according to claim 1 in which $R^1$ and $R^2$ are each $C_{1-10}$ alkyl, $C_{3-10}$ cycloalkyl-$C_{1-10}$ alkyl, optionally substituted phenyl-$C_{1-10}$ alkyl, $C_{1-10}$ alkoxy-$C_{1-10}$ alkyl, optionally substituted heterocyclyl-$C_{1-10}$ alkyl, optionally substituted phenyl fused to $C_{5-10}$ cycloalkyl or [optionally substituted phenyl $(CH_2)_n]_2$-$C_{1-10}$ alkyl.

5. A compound according to claim 1 in which $R^1$ and $R^2$ are each $C_{1-10}$ alkyl, $C_{3-10}$ cycloalkyl-$C_{1-4}$ alkyl, phenyl-$C_{1-4}$ alkyl, diphenyl $C_{1-4}$ alkyl, $C_{1-4}$ alkoxy-$C_{1-4}$ alkyl, or 9-xanthyl-$C_{1-4}$ alkyl.

6. A compound according to claim 1 in which $R^1$ and $R^2$ are each methyl, ethyl, propyl, butyl, pentyl, hexyl, heptyl, octyl, nonyl, methoxymethyl, methoxyethyl, ethoxymethyl, ethoxyethyl, butoxyethyl, benzyl, phenethyl, diphenylmethyl, diphenylethyl and 9-xanthylmethyl.

7. A compound according to claim 1 in which $R^1$ is $C_{1-6}$ alkyl and $R^2$ is 9-xanthylmethyl.

8. A compound selected from (1SR, 2SR, 3SR) 3-Methyl-α-methyl-2-carboxycyclopropyl glycine, (1SR, 2SR, 3SR) 3-Methyl-α-phenylethyl-2-carboxycyclopropyl glycine, (1SR, 2SR, 3SR) 3-Phenylethyl-α-phenylethyl-2-carboxycyclopropyl glycine, (1SR, 2SR, 3SR) 3-Pentyl-α-phenylethyl-2-carboxycyclopropyl glycine, (1SR, 2SR, 3SR) 3-Nonyl-α-phenylethyl-2-carboxycyclopropyl glycine, (1RS, 2SR, 3SR) 3-Nonyl-α-phenylethyl-2-carboxycyclopropyl glycine, (1SR, 2SR, 3SR) 3-Methyl-α-9-xanthylmethyl-2-carboxycyclopropyl glycine, (1SR, 2SR, 3SR) 3-Ethyl-α-9-xanthylmethyl-2-carboxycyclopropyl glycine, (1SR, 2SR, 3SR) 3-Propyl-α-9-xanthylmethyl-2-carboxycyclopropyl glycine, (1SR, 2SR, 3SR) 3-Butyl-α-9-xanthylmethyl-2-carboxycyclopropyl glycine, (1SR, 2SR, 3SR) 3-Pentyl-α-9-xanthylmethyl-2-carboxycyclopropyl glycine, (1SR, 2SR, 3SR) 3-Hexyl-α-9-xanthylmethyl-2-carboxycyclopropyl glycine, (1SR, 2SR, 3SR) 3-Nonyl-α-9-xanthylmethyl-2-carboxycyclopropyl glycine, (1SR, 2SR, 3SR) 3-Phenylethyl-α-9-xanthylmethyl-2-carboxycyclopropyl glycine, (1SR, 2SR, 3SR) 3-isoButyl-α-9-xanthylmethyl-2-carboxycyclopropyl glycine, (2S,1'R, 2'R,3'R)-2-(2'-carboxy-3'-methylcyclopropyl)glycine (2S, 1'S,2'S,3'S)-2-(2'-carboxy-3'-methylcyclopropyl)glycine (2S,1'R,2'R,3'R)-2-(2'-carboxy-3'-ethylcyclopropyl)glycine (2S,1'S,2'S,3'S) 2-(2'-carboxy-3'-ethylcyclopropyl)glycine (2S,1'R,2'R,3'R)-2-(2'-carboxy-3'-propylcyclopropyl) glycine (2S,1'S,2'S,3'S)-2-(2'-carboxy-3'-propylcyclopropyl) glycine.

9. A pharmaceutical formulation comprising a compound according to, claim 1 or a pharmaceutically acceptable salt or ester thereof, together with a pharmaceutically acceptable diluent or carrier therefor.

10. A process for preparing a compound of formula (I), or a pharmaceutically acceptable salt thereof as defined in claim 1 which comprises:

(a) hydrolyzing a compound of formula

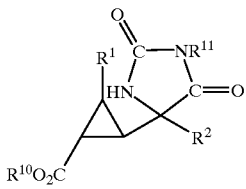

(II)

in which $R^{10}$ and $R^{11}$ each represent hydrogen, a $C_{1-4}$ alkyl group, a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (b) deprotecting a compound of formula

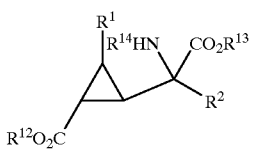

(III)

in which one or both of $R^{12}$ and $R^{13}$ is a carboxyl protecting group, and the other is hydrogen, and $R^{14}$ is hydrogen or an amine protecting group;

followed when necessary by recovering a diastereomer or isomer of the compound, or forming a pharmaceutically acceptable ester or pharmaceutically acceptable salt thereof.

11. A process for preparing a compound of formula (I) or a pharmaceutically acceptable salt thereof as defined in claim 1 where $R^2$ is H, which comprises:

(a) hydrolyzing a compound of formula (II')

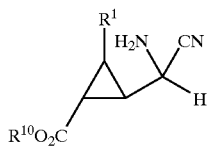

II' in which $R^{10}$ represents hydrogen, a $C_{1-4}$ alkyl group, a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (b) deprotecting a compound of formula (III')

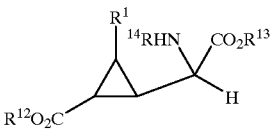

III' in which one or both of $R^{12}$ and $R^{13}$ is a carboxyl protecting group, and the other is hydrogen, and $R^{14}$ is hydrogen or an amine protecting group;

followed when necessary by recovering a diastereomer or isomer of the compound, or forming a pharmaceutically acceptable ester or pharmaceutically acceptable salt thereof.

12. A method of treating an animal suffering from or susceptible to a disorder of the central nervous system, which comprises administering a compound of formula I according to claim 1, or a pharmaceutically acceptable salt or ester thereof.

13. A method as claimed in claim 12, in which the animal is a human.

* * * * *